US008604062B2

(12) United States Patent
Dott et al.

(10) Patent No.: US 8,604,062 B2
(45) Date of Patent: Dec. 10, 2013

(54) PROCESS FOR THE PREPARATION OF ISOXAZOLYL-METHOXY NICOTINIC ACIDS

(71) Applicant: Hoffmann-La Roche Inc., Nutley, NJ (US)

(72) Inventors: Pascal Dott, Rixheim (FR); Steven Paul Hanlon, Bottmingen (CH); Stefan Hildbrand, Gelterkinden (CH); Hans Iding, Rheinfelden (DE); Andrew Thomas, Binningen (CH); Pius Waldmeier, Wegenstetten (CH)

(73) Assignee: Hoffman-La Roche Inc., Nutley, NJ (US)

(*) Notice: Subject to any disclaimer, the term of this patent is extended or adjusted under 35 U.S.C. 154(b) by 0 days.

(21) Appl. No.: 13/650,202

(22) Filed: Oct. 12, 2012

(65) Prior Publication Data

US 2013/0102778 A1   Apr. 25, 2013

(30) Foreign Application Priority Data

Oct. 20, 2011 (EP) .................................... 11185992

(51) Int. Cl.
*A01N 43/40* (2006.01)
*A61K 31/44* (2006.01)
*C07D 413/00* (2006.01)
*C07D 401/00* (2006.01)
*C07D 211/78* (2006.01)
*C07D 211/84* (2006.01)

(52) U.S. Cl.
USPC ........... 514/340; 514/277; 514/344; 514/345; 546/272.1; 546/275.1; 546/286; 546/290

(58) Field of Classification Search
USPC ........................................................ 546/275
See application file for complete search history.

(56) References Cited

U.S. PATENT DOCUMENTS

| 2007/0066668 A1 | 3/2007 | Buettelmann et al. |
| 2007/0082936 A1 | 4/2007 | Buettelmann et al. |
| 2007/0161686 A1 | 7/2007 | Buettelmann et al. |

FOREIGN PATENT DOCUMENTS

| WO | 00/08001 | 2/2000 |
| WO | 03/099793 | 12/2003 |
| WO | 2004/024691 | 3/2004 |
| WO | 2005/113519 | 12/2005 |
| WO | 2006/037480 | 4/2006 |
| WO | 2007/002635 | 1/2007 |
| WO | 2007/039389 | 4/2007 |
| WO | 2009/071464 | 6/2009 |
| WO | 2009/071476 | 6/2009 |
| WO | 2009/071477 | 6/2009 |
| WO | 2010/112475 | 10/2010 |
| WO | 2010/127978 | 11/2010 |

OTHER PUBLICATIONS

Maité Sylla-Iyarreta Veitía, Pierre Louis Brun, Pierre Jorda, Annie Falguières, Clotilde Ferroud Tetrahedron: Asymmetry 20 (2009) 2077-2089.*
Albert J. DelMonte, Yu Fan, Kevin P. Girard, Gregory S. Jones, Robert E. Waltermire, Victor Rosso, and Xuebao WangOrganic Process Research & Development 2011, 15, 64-72.*
Practical Process Research & Development, Neal G.Anderson, Academic Press, 2000.*
Fernando Cardenas, Emilio. Alvarez, Maria-Soledad. de Castro-Alvarez, Jose-Maria. Sanchez-Montero, Manuel Valmaseda, Steve W. Elson, Jose-Vicente. Sinisterra, Journal of Molecular Catalysis B: Enzymatic 14 (2001) 111-123.*
Greene's Protective Groups in Organic Synthesis, Fourth Edition, by Peter G. M. Wuts and Theodora W. Greene 2007 John Wiley & Sons, Inc.*
DiCosimo, R. in Biocatalysis in the Pharmaceutical and Biotechnology Industries, Patel, R. N. Ed. 1st ed, CRC Press, New York, 2006, chapter 1, pp. 1_26.*
"Biological Buffers" Published by AppliChem GmbH, Darmstadt, 2008.*
A. Banerjee, R. Sharma, U.C. Banerjee, Appl Microbiol Biotechnol (2002) 60:33-44.*
McCauley et al., American Journal of Medical Genetics 131B:51-59 ( 2004).
Papdimitriou, G. et al. Neuropsychobiology 43(3):141-144 ( 2001).
Fernandez et al., Nature Neuroscience 10(4):411-413 (Apr. 2007).
Solis-Anez et al., "Autism, chromosome 15 and the GAbaergic dysfunction hypothesis" Invest. Clin. (Abstract attached.), 48(4):529-541 (Dec. 2007).
(International Search Report PCT/EP2012/070521 Nov. 15, 2012).
Otani, K. et al., Neuroscience Letters 381:108-11 ( 2005).
Cui, Y et al., Cell 135:549-560 (Oct. 31, 2008).
Rueda, N. et al., Neuroscience Letters 433:22-27 ( 2008).
DeLong, R., Autism 11(2):135-147 ( 2007).
Felix et al., Journal of Organic Chemistry 60:3907-3909 ( 1995).
(Chilean Office Action in Corres, App.. CL 3591-08 May 10, 2011).
(Translation of Jap. Off Act in Corres Jap Appl. 2010536409 Oct. 30, 2012).
McNamara et al., Psychobiology 21:101-108 ( 1993).
(International Search Report for PCT/EP2008/066225 Feb. 25, 2009).

* cited by examiner

*Primary Examiner* — John Mabry
*Assistant Examiner* — Daniel Carcanague

(57) ABSTRACT

The present invention relates to a process for the preparation of a compound of formula (I)

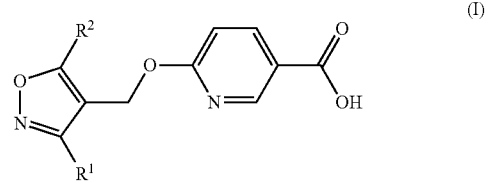

wherein $R^1$ and $R^2$ are as defined herein, which is useful as an intermediate in the preparation of active pharmaceutical compounds.

54 Claims, No Drawings

PROCESS FOR THE PREPARATION OF ISOXAZOLYL-METHOXY NICOTINIC ACIDS

PRIORITY TO RELATED APPLICATION(S)

This application claims the benefit of European Patent Application No. 11185992.2 filed Oct. 20, 2011, which is hereby incorporated by reference in its entirety.

FIELD OF THE INVENTION

The present invention relates to a process for the preparation of an isoxazolyl-methoxy-nicotinic acid compound which is useful as an intermediate in the preparation of active pharmaceutical compounds.

SUMMARY OF THE INVENTION

The present invention provides a process for the preparation of a compound of formula (I)

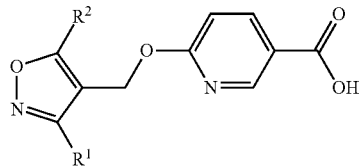

(I)

or pharmaceutically acceptable salts thereof, which comprises the reaction of a compound of formula (II)

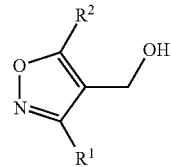

(II)

with a compound of formula (III)

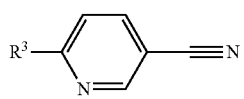

(III)

to a compound of formula (IV)

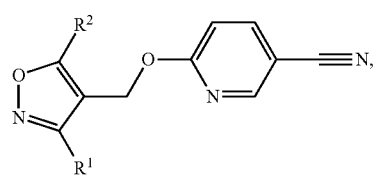

(IV)

followed by the reaction of the compound of formula (IV) to a compound of formula (I) or pharmaceutically acceptable salts thereof, wherein $R^1$, $R^2$ and $R^3$ are as described herein.

Present invention features a number of relevant advantages as compared to standard processes known in the art:

(1) The overall yield for the production of compound of formula (I) is considerably improved.

(2) The selectivity of the coupling reaction of a compound of formula (II) with a compound of formula (III) to a compound of formula (IV) is significantly improved. The increased selectivity is mainly due to the formation of a significantly reduced amount of ether by-product of formula (X) (maximally 1%), as compared to other modes of addition and other bases, which yield typically more than 5% of ether by-product of formula (X).

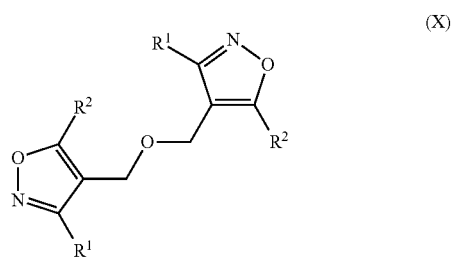

(X)

(3) The hitherto required chromatographic purification of compound of formula (IV) is no longer necessary and hence allows for preparation of compounds of formula (I) on technical scale.

(4) As compared to previously described methods of producing compounds of formula (I) wherein a compound of formula (II) is coupled to the corresponding 2-chloro pyridine nicotinic acid ester followed by saponification, the method of present invention features a significantly increased selectivity.

(5) The present invention allows for a telescoped process for the reaction of a compound of formula (II) with a compound of formula (III) to a compound of formula (IV), and without isolating it further reacting the compound of formula (IV) to a compound of formula (I) in high yields (80-85%) and with a purity of >99% (wt/wt). A telescoped process is particularly advantageous for industrial processes due to a reduced number of workup steps and workup time, increased overall yield, hence improved throughput and cost-efficiency, enhanced operator safety, as well as reduced handling of solvents and thus improved environment-friendliness.

(6) The present invention further allows for a mild enzymatic hydrolysis of compounds of formula (IV) to deliver compounds of formula (I) by conventional extraction.

DETAILED DESCRIPTION OF THE INVENTION

The present invention relates to a process for the preparation of an isoxazolyl-methoxy-nicotinic acid compound which is useful as an intermediate in the preparation of active pharmaceutical compounds.

The present invention provides a process for the preparation of a compound of formula (I)

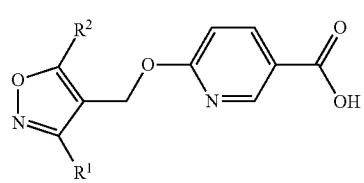

(I)

or pharmaceutically acceptable salts thereof, which comprises the reaction of a compound of formula (II)

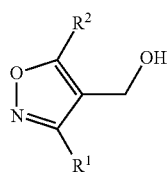

(II)

with a compound of formula (III)

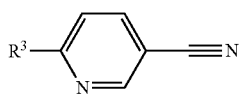

(III)

to a compound of formula (IV)

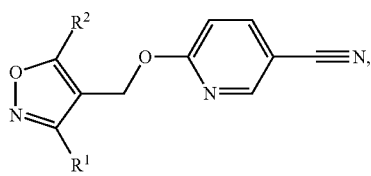

(IV)

followed by the reaction of the compound of formula (IV) to a compound of formula (I) or pharmaceutically acceptable salts thereof, wherein $R^1$, $R^2$ and $R^3$ are as described herein.

DEFINITIONS

Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below.

All publications, patent applications, patents, and other references mentioned herein are incorporated by reference in their entirety.

The nomenclature used in this application is based on IUPAC systematic nomenclature, unless indicated otherwise.

Any open valency appearing on a carbon, oxygen, sulfur or nitrogen atom in the structures herein indicates the presence of hydrogen, unless indicated otherwise.

The definitions described herein apply irrespective of whether the terms in question appear alone or in combination. It is contemplated that the definitions described herein may be appended to form chemically-relevant combinations, such as e.g. "heterocycloalkylaryl", "haloalkylheteroaryl", "arylalkylheterocycloalkyl", or "alkoxyalkyl". The last member of the combination is the radical which is binding to the rest of the molecule. The other members of the combination are attached to the binding radical in reversed order in respect of the literal sequence, e.g. the combination arylalkyl refers to an alkyl-radical which is substituted by an aryl.

The term "moiety" refers to an atom or group of chemically bonded atoms that is attached to another atom or molecule by one or more chemical bonds thereby forming part of a molecule. For example, the variables $R^1$ and $R^2$ of formula (I) refer to moieties that are attached to the core structure of formula (I) by a covalent bond.

When indicating the number of substituents, the term "one or more" refers to the range from one substituent to the highest possible number of substitution, i.e. replacement of one hydrogen up to replacement of all hydrogens by substituents.

The term "optional" or "optionally" denotes that a subsequently described event or circumstance may but need not occur, and that the description includes instances where the event or circumstance occurs and instances in which it does not.

The term "substituent" denotes an atom or a group of atoms replacing a hydrogen atom on the parent molecule.

The term "substituted" denotes that a specified group bears one or more substituents. Where any group may carry multiple substituents and a variety of possible substituents is provided, the substituents are independently selected and need not to be the same. The term "unsubstituted" means that the specified group bears no substituents. The term "optionally substituted" means that the specified group is unsubstituted or substituted by one or more substituents, independently chosen from the group of possible substituents. When indicating the number of substituents, the term "one or more" means from one substituent to the highest possible number of substitution, i.e. replacement of one hydrogen up to replacement of all hydrogens by substituents.

The term "pharmaceutically acceptable esters" denotes derivatives of the compounds of present invention, in which a carboxy group has been converted to an ester, wherein carboxy group means —C(O)O—. Methyl-, ethyl-, methoxymethyl-, methylthiomethyl-, and pivaloyloxymethylesters are examples of such suitable esters. The term "pharmaceutically acceptable esters" furthermore embraces derivatives of the compounds of present invention in which hydroxy groups have been converted to the corresponding esters with inorganic or organic acids such as nitric acid, sulfuric acid, phosphoric acid, citric acid, formic acid, maleic acid, acetic acid, succinic acid, tartaric acid, methanesulfonic acid, or p-toluenesulfonic acid, and which are non toxic to living organisms.

The term "pharmaceutically acceptable salts" denotes salts which are not biologically or otherwise undesirable. Pharmaceutically acceptable salts include both acid and base addition salts.

The term "pharmaceutically acceptable acid addition salt" denotes those pharmaceutically acceptable salts formed with inorganic acids such as hydrochloric acid, hydrobromic acid, sulfuric acid, nitric acid, carbonic acid, phosphoric acid, and organic acids selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, maloneic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, p-toluenesulfonic acid, and salicyclic acid. The term "pharmaceutically acceptable base addition salt" denotes those pharmaceutically acceptable salts formed with an organic or inorganic base. Examples of acceptable inorganic bases include sodium, potassium, ammonium, calcium, magnesium, iron, zinc, copper, manganese, and aluminum salts. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, and polyamine resins.

The term "halo", "halogen", and "halide" are used interchangeably herein and denote fluoro, chloro, bromo, or iodo, particularly fluoro and chloro, most particularly fluoro.

The term "alkyl" denotes a monovalent linear or branched saturated hydrocarbon group of 1 to 12 carbon atoms. In particular embodiments, alkyl has 1 to 7 carbon atoms, and in more particular embodiments 1 to 4 carbon atoms. Examples of alkyl include methyl, ethyl, propyl, isopropyl, n-butyl, iso-butyl, sec-butyl, or tert-butyl. Particular examples of alkyl are methyl, ethyl, n-propyl and iso-propyl, most particularly methyl.

The term "alkoxy" denotes a group of the formula —O—R', wherein R' is an alkyl group. Examples of alkoxy moieties include methoxy, ethoxy, isopropoxy, and tert-butoxy.

The term "haloalkyl" denotes an alkyl group wherein at least one of the hydrogen atoms of the alkyl group has been replaced by same or different halogen atoms, particularly fluoro atoms. Examples of haloalkyl include monofluoro-, difluoro- or trifluoro-methyl, -ethyl or -propyl, for example 3,3,3-trifluoropropyl, 2-fluoroethyl, 2,2,2-trifluoroethyl, fluoromethyl, or trifluoromethyl. The term "perhaloalkyl" denotes an alkyl group where all hydrogen atoms of the alkyl group have been replaced by the same or different halogen atoms. Particular example of haloalkyl is trifluoroethyl.

The term "hydroxyalkyl" denotes an alkyl group wherein at least one of the hydrogen atoms of the alkyl group has been replaced by a hydroxy group. Examples of hydroxyalkyl include hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 2-hydroxy-1-hydroxymethylethyl, 2,3-dihydroxybutyl, 3,4-dihydroxybutyl or 2-(hydroxymethyl)-3-hydroxypropyl. Particular example of hydroxyalkyl is hydroxypropyl.

The term "cycloalkyl" denotes a monovalent saturated monocyclic or bicyclic hydrocarbon group of 3 to 10 ring carbon atoms. In particular embodiments cycloalkyl denotes a monovalent saturated monocyclic hydrocarbon group of 3 to 8 ring carbon atoms. Bicyclic means consisting of two saturated carbocycles having one or more carbon atoms in common. Particular cycloalkyl groups are monocyclic. Examples for monocyclic cycloalkyl are cyclopropyl, cyclobutanyl, cyclopentyl, cyclohexyl or cycloheptyl. Examples for bicyclic cycloalkyl are bicyclo[2.2.1]heptanyl, or bicyclo[2.2.2]octanyl. Particular example of cycloalkyl is cyclopropyl.

The term "cycloalkylalkyl" denotes an alkyl group wherein at least one of the hydrogen atoms of the alkyl group is replaced by a cycloalkyl group. Examples of cycloalkylalkyl include cyclopropylmethyl, cyclopropylethyl, cyclobutylpropyl and cyclopentylethyl. Particular example of cycloalkylalkyl is cyclopropylmethyl.

The term "heterocycloalkyl" denotes a monovalent saturated or partly unsaturated mono- or bicyclic ring system of 3 to 9 ring atoms, comprising 1, 2, or 3 ring heteroatoms selected from N, O and S, the remaining ring atoms being carbon. In particular embodiments, heterocycloalkyl is a monovalent saturated monocyclic ring system of 4 to 7 ring atoms, comprising 1, 2, or 3 ring heteroatoms selected from N, O and S, the remaining ring atoms being carbon. Examples for monocyclic saturated heterocycloalkyl are aziridinyl, oxiranyl, azetidinyl, oxetanyl, pyrrolidinyl, tetrahydrofuranyl, tetrahydro-thienyl, pyrazolidinyl, imidazolidinyl, oxazolidinyl, isoxazolidinyl, thiazolidinyl, piperidinyl, tetrahydropyranyl, tetrahydrothiopyranyl, piperazinyl, morpholinyl, thiomorpholinyl, 1,1-dioxo-thiomorpholin-4-yl, azepanyl, diazepanyl, homopiperazinyl, or oxazepanyl. Examples for bicyclic saturated heterocycloalkyl are 8-aza-bicyclo[3.2.1]octyl, quinuclidinyl, 8-oxa-3-aza-bicyclo[3.2.1]octyl, 9-aza-bicyclo[3.3.1]nonyl, 3-oxa-9-aza-bicyclo[3.3.1]nonyl, or 3-thia-9-aza-bicyclo[3.3.1]nonyl. Examples for partly unsaturated heterocycloalkyl are dihydrofuryl, imidazolinyl, dihydro-oxazolyl, tetrahydro-pyridinyl, or dihydropyranyl. Particular examples of heterocycloalkyl are pyrrolidinyl, thiazolidinyl, piperidinyl, tetrahydropyranyl, morpholinyl, dioxo-thiomorpholinyl or thiomorpholinyl, most particularly dioxo-thiomorpholinyl.

The term "aromatic" denotes the conventional idea of aromaticity as defined in the literature, in particular in IUPAC—Compendium of Chemical Terminology, 2nd, A. D. McNaught & A. Wilkinson (Eds). Blackwell Scientific Publications, Oxford (1997).

The term "aryl" denotes a monovalent aromatic carbocyclic mono- or bicyclic ring system comprising 6 to 10 carbon ring atoms. Examples of aryl moieties include phenyl and naphthyl, particularly phenyl.

The term "heteroaryl" denotes a monovalent aromatic heterocyclic mono- or bicyclic ring system of 5 to 12 ring atoms, comprising 1, 2, 3 or 4 heteroatoms selected from N, O and S, the remaining ring atoms being carbon. Examples of heteroaryl moieties include pyrrolyl, furanyl, thienyl, imidazolyl, oxazolyl, thiazolyl, triazolyl, oxadiazolyl, thiadiazolyl, tetrazolyl, pyridinyl, pyrazinyl, pyrazolyl, pyridazinyl, pyrimidinyl, triazinyl, azepinyl, diazepinyl, isoxazolyl, benzofuranyl, isothiazolyl, benzothienyl, indolyl, isoindolyl, isobenzofuranyl, benzimidazolyl, benzoxazolyl, benzoisoxazolyl, benzothiazolyl, benzoisothiazolyl, benzooxadiazolyl, benzothiadiazolyl, benzotriazolyl, purinyl, quinolinyl, isoquinolinyl, quinazolinyl, or quinoxalinyl. Particular examples of heteroaryl are isoxazolyl, pyrazolyl, pyridinyl, or 5,6-Dihydro-8H-[1,2,4]triazolo[4,3-a]pyrazin-7-yl.

The term "telescoped process" denotes a process in which one or several intermediates are not isolated from the reaction mixture and purified but directly converted by a chemical transformation to the next intermediate or final product.

The term "concentration to dryness" denotes evaporation of a solvent or a solvent mixture at room or elevated temperatures under reduced or atmospheric pressure until no more solvent or solvent mixture is distilled off.

The term "biocatalyst" denotes a catalyst of biological origin, such as protein enzymes, to perform chemical transformations on organic compounds. Both, enzymes that have been isolated and enzymes still residing inside whole microbial cells are employed as biocatalysts.

The term "halogenating agent" denotes a reagent that incorporates a halogen atom into a molecule in substitution of a hydrogen atom.

The term "chlorinating agent" denotes a reagent that incorporates a chlorine atom into a molecule in substitution of a hydrogen atom. An example of a chlorinating agent is NCS.

The IUPAC lamda convention (W. H. Powell, *Pure & Appl. Chem.* (1984) 56(6): 769-778) provides a general method for indicating nonstandard valence states of heteroatoms in a molecule. The bonding number "n" of a heteroatom is the sum of the total number of valence bonds to adjacent atoms, if any, and the number of attached hydrogen atoms. The bonding number of a heteroatom is standard when it has the value given in the following table:

| | |
|---|---|
| n = 4: | C, Si, Ge, Sn, Pb; |
| n = 3: | B, N, P, As, Sb, Bi |
| n = 2: | O, S, Se, Te, Po; |
| n = 1; | F, Cl, Br, I, At. |

A non-standard bonding number of a (neutral) heteroatom is indicated by the symbol "$\lambda^n$", where "n" is the bonding number. If the locant, the number indicating the position within the molecule, for a heteroatom with a nonstandard bonding number is used, the $\lambda^n$ symbol is cited immediately after this locant.

The terms (1,1-dioxo-1$\lambda^6$-thiomorpholin-4-yl)-, (1,1-dioxo-1λ,6-thiomorpholin-4-yl)-, (1,1-dioxo-1,6-thiomorpholin-4-yl)-, and (1,1-dioxo-thiomorpholin-4-yl)- are used herein interchangeably to denote a thiomorpholinyl-radical wherein the sulfur ringatom is substituted with two oxo groups of the structure as follows:

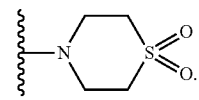

ABBREVIATIONS USED

CDI=1,1'-carbonyldiimidazole
DIPEA=N,N-diisopropylethylamine
DMAP=4-(Dimethylamino)-pyridine
DMF=N,N-dimethylformamide
EDAC=1-ethyl-3-(3-dimethylaminopropyl) carbodiimide hydrochloride
HOBt=N1-hydroxybenzotriazole
LiOtBu=lithium tert-butoxide
$Me_3Al$=trimethylaluminium
MeTHF=methyltetrahydrofuran
MTBE=methyl tert-butyl ether
NaOtBu=sodium tert-butoxide
NCS=N-chlorosuccinimide
TBTU=2-(1H-benzotriazole-1-yl)-1,1,3,3-tetramethyluronium tetrafluoroborate
TBD=1,5,7-triazabicyclo[4.4.0]dec-5-ene
TEA=triethylamine
THF=tetrahydrofuran

DESCRIPTION OF THE SCHEMES OF THE INVENTION

Scheme 1
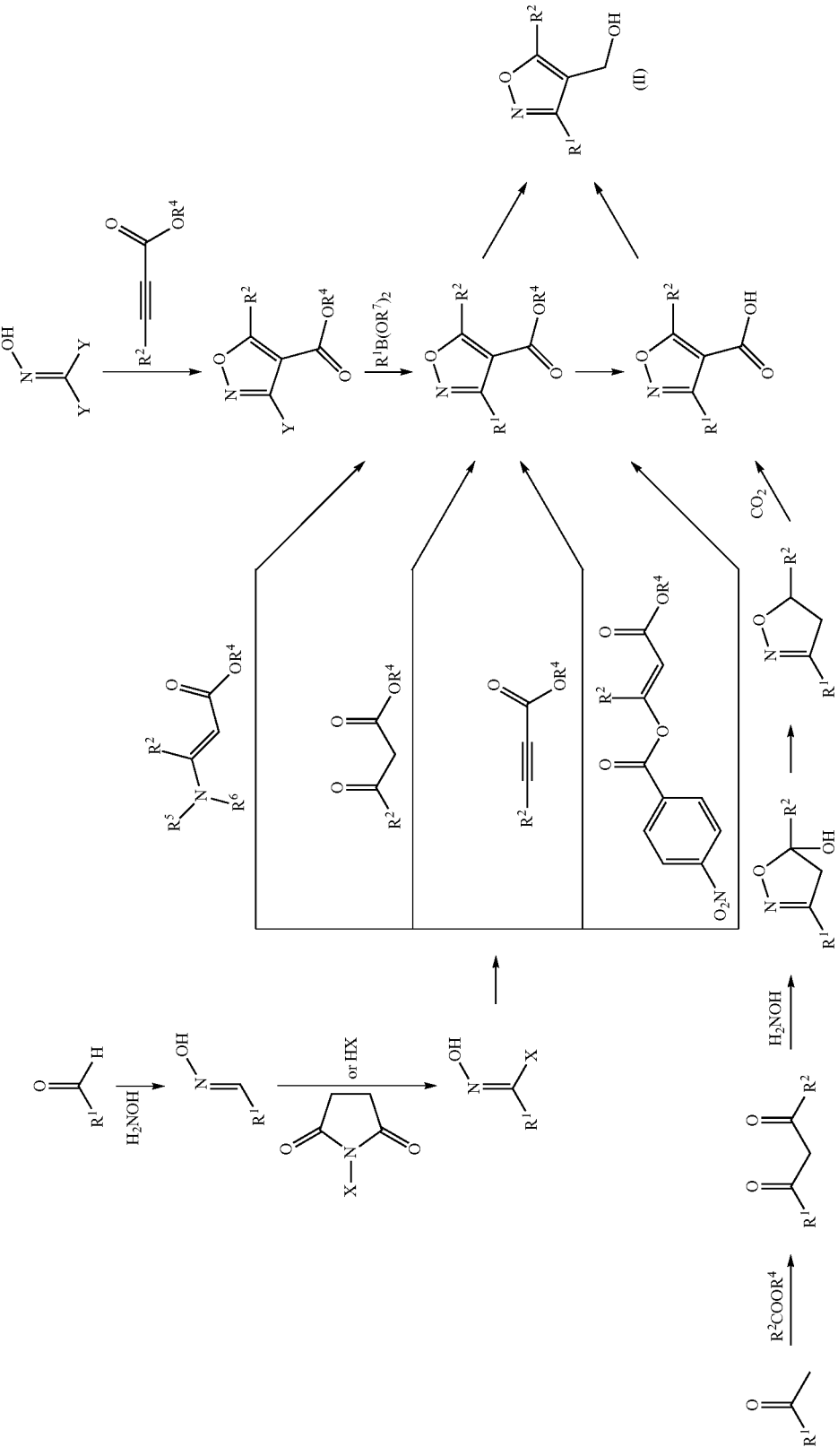

Compounds of formula (II) can be prepared as described e.g. in WO 2009/071476 or WO 2010/127978. In particular, compounds of formula (II) can be prepared according to Schemes 1 to 6, wherein $R^1$, and $R^2$ are as described herein and $R^4$, $R^5$, and $R^6$ are independently alkyl, particularly ethyl or methyl; or $R^5$ and $R^6$ together with the nitrogen to which they are attached to form a heterocycloalkyl, particularly pyrrolidinyl; X is halo, particularly chloro; and Y is halo, particularly bromo.

In accordance to Scheme 2, a compound of formula (1), wherein $R^1$ is as described herein, can be reacted with hydroxylamine hydrochloride in a solvent, such as ethanol and water in the presence of a base, such as aqueous sodium hydroxide to give a compound of formula (2). A compound of formula (2) can be reacted with a halogenating agent, particularly a chlorinating agent, more particularly N-chlorosuccinimide (NCS), and optionally a catalyst, particularly pyridine, in a solvent, such as DMF, dichloromethane or chloroform, to give a compound of formula (3), wherein $R^1$ and X are as described herein, particularly X is chloro. Alternatively a compound of formula (2) can be reacted with a halogenating agent, particularly a chlorinating agent, more particularly hydrogenchloride, and potassium monopersulfate triple salt in a solvent, particularly DMF, to give a compound of formula (3), wherein $R^1$ and X are as described herein, particularly X is chloro.

Scheme 2

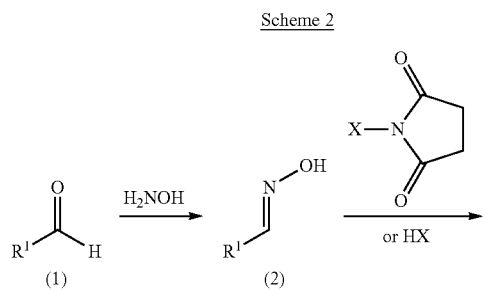

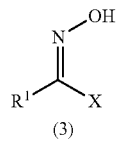

(3)

Optionally, after the reaction of a compound of formula (2) to a compound of formula (3), as described above, the compound of formula (3) does not need to be worked up and isolated for subsequent reaction to a compound of formula (12), as described below. The reaction of a compound of formula (2) to a compound of formula (12) via a compound of formula (3) can also be performed in a one-pot synthesis.

In accordance to Scheme 3, a compound of formula (3) can be reacted with a compound of formula (4), wherein $R^2$, $R^4$, $R^5$ and $R^6$ are as defined herein, particularly $R^4$ is methyl or ethyl and $R^5$ and $R^6$ together with the nitrogen to which they are attached to form a heterocycloalkyl, particularly pyrrolidinyl, also particularly $R^4$ is ethyl and $R^5$ and $R^6$ are both methyl, in the presence of a base, such as triethylamine or sodium hydrogen carbonate, in a solvent, such as chloroform, diethylether, tert-butanol, or DMF, to yield a compound of formula (12), wherein $R^1$, $R^2$, and $R^4$ are as described herein. Alternatively a compound of formula (5) wherein $R^2$ and $R^4$ are as described herein, particularly $R^4$ is methyl, can be reacted with sodium in a solvent, such as methanol, and then a solution of a compound of formula (3) in a solvent, such as methanol, can be added to yield a compound of formula (12), wherein $R^1$, $R^2$, and $R^4$ are as described herein. Compounds of formula (4) can conventionally be obtained from compounds of formula (5) by reaction with the corresponding secondary amine e.g. pyrrolidine. Alternatively a compound of formula (3) can be reacted with a compound of formula (6), wherein $R^2$ and $R^4$ are as defined herein, particularly $R^4$ is methyl or ethyl, in the presence of a base, such as triethylamine, in a solvent, such as diethylether or ethanol, to yield a compound of formula (12), wherein $R^1$, $R^2$, and $R^4$ are as described herein. Alternatively a compound of formula (3) can be reacted with a compound of formula (7), wherein $R^2$ and $R^4$ are as defined herein, particularly $R^4$ is methyl, in a solvent, such as dichloromethane, in the presence of a base, such as triethylamine, Scheme 3

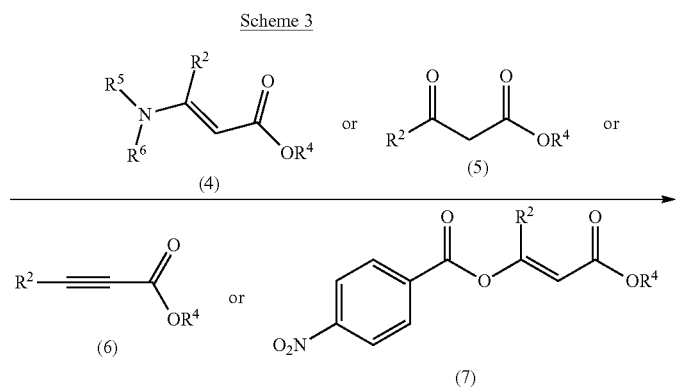

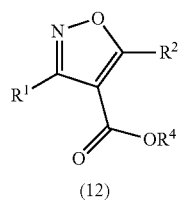

(12)

According to Scheme 4, a compound of formula (8), wherein Y is as described herein, particularly Y is bromo, can be reacted with a compound of formula (9), wherein $R^2$ and $R^4$ are as described herein, particularly $R^4$ is ethyl, in the presence of a base, such as potassium carbonate, in a solvent, such as dichloromethane, to give a compound of formula (10), wherein $R^2$, $R^4$ and Y are as described herein. A compound of formula (10) can be reacted with a compound of formula (11), wherein $R^1$ is as described herein and $R^7$ is hydrogen or alkyl, in the presence of a catalyst, such as a Pd catalyst, particularly $Pd(PPh_3)_4$, in a coupling reaction, particularly in a Suzuki coupling reaction, to give a compound of formula (12).

Scheme 4

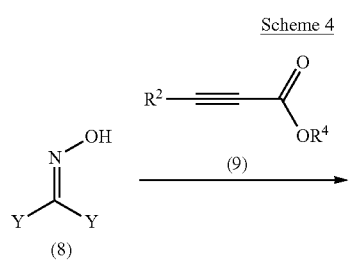

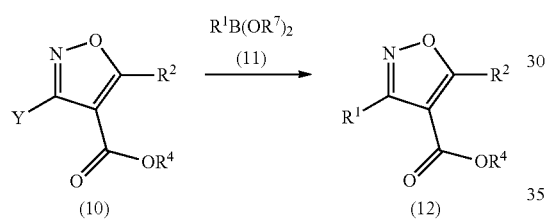

According to Scheme 5, a compound of formula (13), wherein $R^1$ is as described herein, can be reacted with a compound of formula (14), wherein $R^2$ and $R^4$ are as described herein, particularly $R^4$ is ethyl, in a solvent, such as tert-butylmethylether, in the presence of a base, such as sodium methoxide, to give a compound of formula (15). A compound of formula (15) can be reacted with hydroxylamine hydrochloride in the presence of a base, such as sodium hydroxide, in a solvent, such as ethanol, to give a compound of formula (16). A compound of formula (16) can be reacted with an acid, such as trifluoroacetic acid, to give a compound of formula (17). A compound of formula (17) can be reacted with a base, such as n-butyllithium (BuLi) and 2,2,6,6-tetramethylpiperidine, in a solvent, such as THF and/or hexane, followed by carbon dioxide, to give a compound of formula (18).

Scheme 5

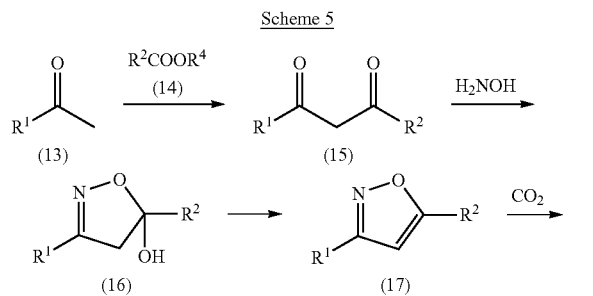

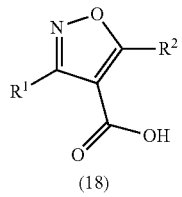

According to Scheme 6, a compound of formula (12) can be reacted with a reducing agent, such as lithiumaluminiumhydride, diisobutylaluminiumhydride (DIBAL-H) or sodium bis(2-methoxyethoxy)aluminumhydride (Red-Al, Vitride), in a solvent, such as THF, to give a compound of formula (II). Alternatively a compound of formula (12) can be reacted with a hydrolyzing agent, such as NaOH or LiOH, in a solvent, such as THF, methanol, ethanol, water, or mixtures thereof, to give a compound of formula (18). A compound of formula (18) can be reacted with a reducing agent, such as lithiumaluminiumhydride, ethylchloroformate in the presence of sodiumborohydride, or sodiumborohydride in the presence of $ZnCl_2$, in a solvent, such as THF, optionally in the presence of a base, such as trimethyl amine, to give a compound of formula (II).

Scheme 6

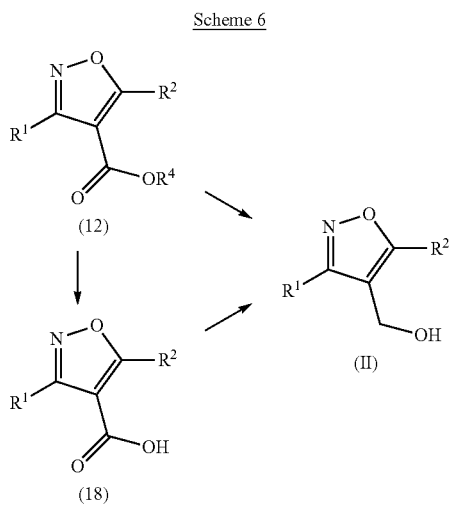

DETAILED DESCRIPTION OF THE INVENTION

In detail, the present invention relates to a process for the preparation of a compound of formula (I) or salts thereof

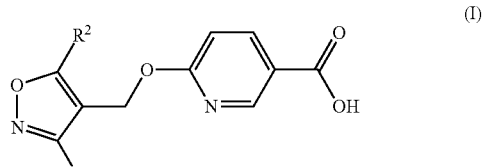

wherein $R^1$ is phenyl optionally substituted by one or more halogen and $R^2$ is hydrogen, alkyl or haloalkyl; which comprises the reaction of a compound of formula (IV)

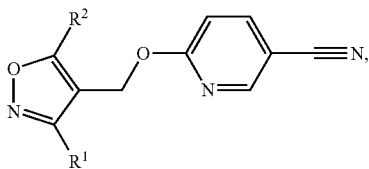

(IV)

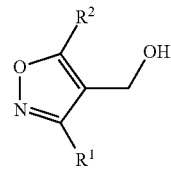

(II)

to a compound of formula (I) or salts thereof.

In one aspect of the invention R¹ is phenyl optionally substituted by one or more halogen.

In one aspect of the invention R¹ is phenyl, or phenyl substituted by one fluoro, or phenyl substituted by one chloro.

In one aspect of the invention R¹ is 4-fluoro-phenyl.

In one aspect of the invention R² is hydrogen, alkyl or haloalkyl.

In one aspect of the invention R² is hydrogen, or methyl.

In one aspect of the invention R² is methyl.

In one aspect of the invention, the reaction of a compound of formula (IV) to a compound of formula (I), wherein R¹ and R² are as described herein, comprises the following reaction steps:

a) hydrolysis of a compound of formula (IV) in a solvent, in the presence of a base; followed by b) removal of impurities by filtration; followed by c) addition of an acid, in a solvent; followed by d) filtration, washing with an alcohol/water mixture and drying of the thereby obtained crystals of a compound of formula (I).

In one aspect of the invention, the solvent employed in step a) is an alcohol/water mixture, particularly a mixture of water with methanol, water with ethanol or water with isopropanol, most particularly a mixture of water with ethanol.

In one aspect of the invention, the base employed in step a) is an alkali metal hydroxide, particularly sodium hydroxide, potassium hydroxide or lithium hydroxide, most particularly sodium hydroxide.

In one aspect of the invention, 7 to 10 eq, more particularly 8 to 9 eq, of base are employed with respect to the compound of formula (IV) in step a).

In one aspect of the invention, step a) takes place at a temperature between 50° C. and 60° C., particularly at a temperature between 50° C. and 55° C.

In one aspect of the invention, step a) takes place during a time period of 12 to 15 hours.

In one aspect of the invention, the impurities removed in step b) are an ether by-product of formula (X).

In one aspect of the invention, the acid employed in step c) is aqueous hydrochloric acid or aqueous sulfuric acid.

In one aspect of the invention, the solvent employed in step c) is water.

In one aspect of the invention, the acid employed in step c) is aqueous hydrochloric acid or aqueous sulfuric acid and the solvent employed in step c) is water.

In one aspect of the invention, the acid employed in step c) is added until the pH value of the solution is below pH 3.

In another embodiment, the present invention relates to a process for the preparation of a compound of formula (I) or salts thereof as described above, wherein the compound of formula (IV) is prepared by reaction of a compound of formula (II)

with a compound of formula (III)

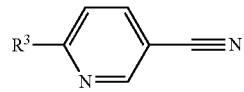

(III)

wherein R³ is a leaving group selected from halogen, —OS(O)₂-alkyl, or —OS(O)₂-aryl, in the presence of a base.

In one aspect of the invention R³ is halogen, —OS(O)₂-alkyl, or —OS(O)₂-aryl.

In one aspect of the invention R³ is chloro, bromo, iodo, methanesulfonate, or toluene-4-sulfonate.

In one aspect of the invention R³ is chloro.

In one aspect of the invention, the reaction of a compound of formula (II) with a compound of formula (III) to a compound of formula (IV), wherein R¹, R² and R³ are as described herein, comprises the following reaction steps:

e) dissolution of a compound of formula (II) together with a compound of formula (III) in a solvent; followed by f) addition of this solution to a suspension of a base in a solvent and reaction; followed by g) neutralization by addition of an acid in a solvent; followed by h) isolation of the compound of formula (IV) by a solvent exchange to alcohol/water and subsequent filtration and drying.

In one aspect of the invention, 0.9 to 1.1 equivalents (eq), more particularly 1.0 to 1.05 eq, of the compound of formula (III) are employed with respect to the compound of formula (II) in step e).

In one aspect of the invention, the solvent employed in step e) is THF or MeTHF, particularly THF.

In one aspect of the invention, the base employed in step f) is sodium hydride or sodium tert-butoxide, particularly sodium hydride.

In one aspect of the invention, 1.3 to 1.7 eq, more particularly 1.4 to 1.6 eq, of base are employed with respect to the compound of formula (II) in step f).

In one aspect of the invention, the suspension of base employed in step f) is a suspension of sodium hydride in THF or MeTHF, particularly in THF.

In one aspect of the invention, the base employed in step f) is sodium hydride or sodium tert-butoxide and the solvent employed in step f) is THF or MeTHF.

In one aspect of the invention, step f) takes place at a temperature between 20° C. and 40° C., particularly at a temperature between 25° C. and 35° C.

In one aspect of the invention, the addition of the solution of a compound of formula (II) and a compound of formula (III) to a suspension of a base in step f) is performed during a time period of 1 to 2 hours.

In one aspect of the invention, the reaction of a compound of formula (II) with a compound of formula (III) in the presence of a base in step f) takes place during a time period of 1 to 3 hours.

In one aspect of the invention, the acid employed in step g) is citric acid.

In one aspect of the invention, the solvent employed in step g) is water.

In one aspect of the invention, the acid employed in step g) is citric acid and the solvent employed in step g) is water.

In one aspect of the invention, step g) takes place at a temperature between 10° C. and 40° C., particularly at a temperature between 20° C. and 30° C.

In one aspect of the invention, in step h) the solvent is exchanged to alcohol/water, particularly to a mixture of water with methanol, water with ethanol or water with isopropanol, most particularly to a mixture of water with ethanol.

Alternatively, compounds of formula (I) can be prepared in a telescoped process through a reaction of a compound of formula (II) with a compound of formula (III) to a compound of formula (IV), followed by directly converting the compound of formula (IV) without isolating it to a compound of formula (I). The crude compound of formula (I) is then purified by washing the aqueous reaction mixture with a solvent, particularly toluene, to remove impurities, such as the mineral oil from NaH and also the ether by-product of formula (X), followed by acidification of the aqueous phase with an acid, particularly sulfuric acid. The compound of formula (I) is then extracted with a solvent, particularly THF and/or toluene and subsequently crystallized from toluene to yield compounds of formula (I).

In one aspect of the invention, the telescoped process wherein a compound of formula (II) is reacted with a compound of formula (III) to a compound of formula (IV), followed by directly converting the compound of formula (IV) without isolating it to a compound of formula (I), wherein $R^1$, $R^2$ and $R^3$ are as described herein, comprises the following reaction steps:

r) dissolution of a compound of formula (II) together with a compound of formula (III) in a solvent; followed by
s) addition of this solution to a suspension of a base in a solvent and reaction; followed by
t) quenching of the reaction; followed by
u) solvent exchange to alcohol/water; followed by
v) treatment with a base, in a solvent; followed by
w) washing the aqueous reaction mixture with a solvent to remove impurities; followed by
x) acidification of the aqueous phase with an acid; followed by
y) extraction of the compound of formula (I) with a solvent; followed by
z) crystallization from a solvent to yield compounds of formula (I).

In one aspect of the invention, 0.9 to 1.1 eq, more particularly 1.0 to 1.05 eq, of the compound of formula (III) are employed with respect to the compound of formula (II) in step r).

In one aspect of the invention, the solvent employed in step r) is THF or MeTHF, particularly THF.

In one aspect of the invention, the base employed in step s) is sodium hydride.

In one aspect of the invention, the suspension of base employed in step s) is a suspension of sodium hydride in THF or MeTHF, particularly in THF.

In one aspect of the invention, 1.3 to 1.7 eq, more particularly 1.4 to 1.6 eq, of base are employed with respect to the compound of formula (II) in step s).

In one aspect of the invention, step s) takes place at a temperature between 20° C. and 40° C., particularly at a temperature between 25° C. and 35° C.

In one aspect of the invention, the addition of the solution of a compound of formula (II) and a compound of formula (III) to a suspension of a base in step s) is performed during a time period of 1 to 2 hours.

In one aspect of the invention, the reaction of a compound of formula (II) with a compound of formula (III) in the presence of a base in step s) takes place during a time period of 1 to 3 hours.

In one aspect of the invention, step t) takes place at a temperature between 10° C. and 40° C., particularly at a temperature between 20° C. and 30° C.

In one aspect of the invention, the reaction is quenched with water in step t).

In one aspect of the invention, the solvent exchange in step u) is performed to alcohol/water, particularly to a mixture of water with methanol, water with ethanol or water with isopropanol, most particularly to a mixture of water with ethanol.

In one aspect of the invention, the base employed in step v) is an alkali metal hydroxide, particularly sodium hydroxide, potassium hydroxide or lithium hydroxide, most particularly sodium hydroxide.

In one aspect of the invention, 7 to 10 eq, more particularly 8 to 9 eq, of base are employed with respect to the compound of formula (IV) in step v).

In one aspect of the invention, the solvent employed in step v) is an alcohol/water mixture, particularly a mixture of water with methanol, water with ethanol or water with isopropanol, most particularly a mixture of water with ethanol.

In one aspect of the invention, the base employed in step v) is sodium hydroxide, potassium hydroxide or lithium hydroxide and the solvent employed in step v) is a mixture of water with methanol, water with ethanol or water with isopropanol.

In one aspect of the invention, step v) takes place at a temperature between 45° C. and 60° C., particularly at a temperature between 50° C. and 55° C.

In one aspect of the invention, step v) takes place during a time period of 12 to 15 hours.

In one aspect of the invention, the solvent employed in step w) is an organic solvent, particularly toluene.

In one aspect of the invention, the impurities removed in step w) are mineral oil from NaH and ether by-product of formula (X).

In one aspect of the invention, the acid employed in step x) is aqueous hydrochloric acid or aqueous sulfuric acid.

In one aspect of the invention, the acid employed in step x) is added until the pH value of the solution is lower than pH 3.3, particularly until the pH value is between 3.0 and 3.3.

In one aspect of the invention, the solvent employed in step y) is an organic solvent, particularly THF, toluene or a mixture of THF/toluene.

In one aspect of the invention, the solvent employed in step z) is an organic solvent, particularly toluene.

Alternatively, compounds of formula (IV) can be converted to compounds of formula (I), wherein $R^1$ and $R^2$ are as described herein, using a biocatalytical process. In detail, a biocatalyst is reacted with compounds of formula (IV) in an aqueous buffer. In the course of the reaction the pH of the reaction mixture is kept constant at the selected value by the addition of a base, particularly by the addition of aqueous NaOH or aqueous KOH-solution.

In one aspect of the invention, a compound of formula (IV) is converted to a compound of formula (I) in a biocatalytical process.

In one aspect of the invention, the biocatalyst employed in the biocatalytical process is a whole microbial cell, particularly microbial strain *Fusarium poae* [ATCC 24668].

In one aspect of the invention, the biocatalyst employed in the biocatalytical process is an enzyme, particularly a nitrilase, more particularly a nitrilase selected from Nit-103, Nit-104, Nit-107, Nit-108, Nit-121, Nit-122, Nit-124 and Nit-127, commercially available from Codexis [former Biocatalytics, 200 Penobscot Drive, Redwood City, Calif. 94063, US]. Particular nitrilases are selected from the group of Nit-104, Nit-107 and Nit-108. Most particular biocatalyst is the nitrilase Nit-107, which is equivalent to nitrilase EC 3.5.5.7 from *Acidovorax facilis* [DuPont; 1007 Market Street, Wilmington, Del. 19898, US].

In one aspect of the invention, 0.1% to 25% (wt/wt), more particularly 0.5% to 5% (wt/wt), of biocatalyst is employed with respect to the compound of formula (IV) in the biocatalytical process.

In one aspect of the invention, the enzymes used as biocatalyst are employed in immobilized form.

In one aspect of the invention, the aqueous buffer used in the biocatalalytical process is a conventional buffer commonly used in biochemistry selected from the group of N,N-bis(2-hydroxyethyl)glycine (Bicine), 4-2-hydroxyethyl-1-piperazineethanesulfonic acid (HEPES), 2-(N-morpholino) ethanesulfonic acid (MES), 3-(N-morpholino) propanesulfonic acid (MOPS), phosphate buffer saline (PBS), piperazine-N,N'-bis(2-ethanesulfonic acid) (PIPES), saline sodium citrate (SSC), 3-{[tris(hydroxymethyl)-methyl]amino}-propanesulfonic acid (TAPS), 2-{[tris(hydroxymethyl)-methyl]-amino}ethanesulfonic acid (TES), N-tris(hydroxymethyl)-methylglycine (Tricine), and tris(hydroxymethyl)-methylamine (TRIS), or mixtures thereof. Particular aqueous buffer is a TRIS buffer. The aqueous buffer is in the range of pH 5-10, particularly pH 5-9, most particularly pH 8-9.

In one aspect of the invention the biocatalytical process takes place at a temperature between 20 and 50° C., particularly at a temperature between 30 and 40° C.

As described herein, compounds of formula (IV) may be used as intermediates in the process for the preparation of compounds of formula (I).

In one aspect, the invention relates to a compound of formula (IV), wherein $R^1$ and $R^2$ are as described herein, with the proviso that when $R^1$ is phenyl then $R^2$ is not methyl, when prepared as an intermediate in the process as described herein.

In one aspect, the invention relates to a process as described herein, wherein the compound of formula (IV) is selected from the group consisting of:
6-(5-Methyl-3-phenyl-isoxazol-4-ylmethoxy)-nicotinonitrile;
6-[3-(3-Fluoro-phenyl)-5-methyl-isoxazol-4-ylmethoxy]-nicotinonitrile;
6-[3-(3-Chloro-phenyl)-5-methyl-isoxazol-4-ylmethoxy]-nicotinonitrile;
6-[3-(4-Fluoro-phenyl)-5-methyl-isoxazol-4-ylmethoxy]-nicotinonitrile;
6-[3-(4-Chloro-phenyl)-isoxazol-4-ylmethoxy]-nicotinonitrile; and
6-[3-(4-Chloro-phenyl)-5-methyl-isoxazol-4-ylmethoxy]-nicotinonitrile.

In one aspect, the invention relates to a process as described herein, wherein the compound of formula (IV) is selected from the group consisting of:
6-[3-(3-Fluoro-phenyl)-5-methyl-isoxazol-4-ylmethoxy]-nicotinonitrile;
6-[3-(3-Chloro-phenyl)-5-methyl-isoxazol-4-ylmethoxy]-nicotinonitrile;
6-[3-(4-Fluoro-phenyl)-5-methyl-isoxazol-4-ylmethoxy]-nicotinonitrile;
6-[3-(4-Chloro-phenyl)-isoxazol-4-ylmethoxy]-nicotinonitrile; and
6-[3-(4-Chloro-phenyl)-5-methyl-isoxazol-4-ylmethoxy]-nicotinonitrile.

In one aspect, the invention relates to a process as described herein, wherein the compound of formula (IV) is 6-[3-(4-Fluoro-phenyl)-5-methyl-isoxazol-4-ylmethoxy]-nicotinonitrile.

In one aspect, the invention relates to a process as described herein, wherein the compound of formula (I) is selected from the group consisting of:
6-(5-Methyl-3-phenyl-isoxazol-4-ylmethoxy)-nicotinic acid;
6-[3-(3-Fluoro-phenyl)-5-methyl-isoxazol-4-ylmethoxy]-nicotinic acid;
6-[3-(3-Chloro-phenyl)-5-methyl-isoxazol-4-ylmethoxy]-nicotinic acid;
6-[3-(4-Fluoro-phenyl)-5-methyl-isoxazol-4-ylmethoxy]-nicotinic acid;
6-[3-(4-Chloro-phenyl)-isoxazol-4-ylmethoxy]-nicotinic acid; and
6-[3-(4-Chloro-phenyl)-5-methyl-isoxazol-4-ylmethoxy]-nicotinic acid; and salts thereof.

In one aspect, the invention relates to a process as described herein, wherein the compound of formula (I) is 6-[3-(4-Fluoro-phenyl)-5-methyl-isoxazol-4-ylmethoxy]-nicotinic acid; or salts thereof.

Compounds of formula (I) may be used as intermediates in the synthesis of valuable active pharmaceutical compounds. In particular, a compound of formula (I) may be used as an intermediate in the synthesis of active pharmaceutical compounds having affinity and selectivity for the GABA A α5 receptor binding site, as described in WO 2009/071476.

In another aspect, the present invention relates to a process for the preparation of a compound of formula (I) as described herein, wherein $R^1$ and $R^2$ are as described herein, further comprising the reaction of a compound of formula (I) or salts thereof with a compound of formula (V) or salts thereof,

wherein $R^8$ and $R^9$ are independently selected from the group of hydrogen, alkyl, haloalkyl, hydroxyalkyl, cycloalkyl, cycloalkylalkyl, heterocycloalkyl, heterocycloalkylalkyl, aryl, arylalkyl, heteroaryl, and heteroarylalkyl, wherein cycloalkyl, heterocycloalkyl, aryl and heteroaryl are optionally substituted with one or more halogen, CN, alkyl, alkoxy, haloalkyl, hydroxyalkyl, hydroxy, or oxo; or $R^8$ and $R^9$ together with the nitrogen to which they are attached to form a heterocycloalkyl or heteroaryl, wherein heterocycloalkyl and heteroaryl are optionally substituted with one or more halogen, CN, alkyl, alkoxy, haloalkyl, hydroxyalkyl, hydroxy, or oxo; with the proviso that $R^8$ and $R^9$ are not both hydrogen; to a compound of formula (VI) or pharmaceutically acceptable salts thereof

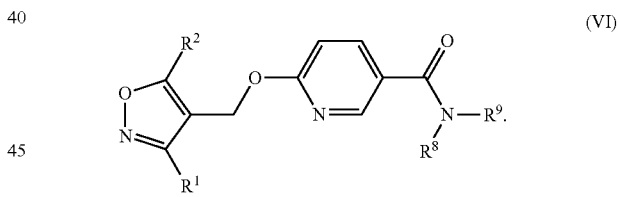

In one aspect, the present invention relates to a process for the preparation of a compound of formula (I) as described herein, wherein $R^1$ and $R^2$ are as described herein, further comprising the reaction of an alkyl ester of compound of formula (I), particularly a methyl ester or ethyl ester of a compound of formula (I) with a compound of formula (V), wherein $R^8$ and $R^9$ are as described herein, to a compound of formula (VI) and pharmaceutically acceptable salts thereof.

In one aspect, the present invention relates to a process for the preparation of a compound of formula (I) as described herein, further comprising the reaction of a compound of formula (I) or salts thereof, in a solvent, such as DMF, in the presence of TBTU and DIPEA, together with a compound of formula (V), in a solvent, such as methanol, to give a compound of formula (VI), wherein $R^1$, $R^2$, $R^8$ and $R^9$ are as described herein.

In one aspect, the present invention relates to a process for the preparation of a compound of formula (I) as described herein, further comprising the reaction of a compound of formula (I) or salts thereof, in a solvent, such as THF, in the presence of HOBT, DIPEA and EDAC, together with a compound of formula (V), to give a compound of formula (VI), wherein $R^1$, $R^2$, $R^8$ and $R^9$ are as described herein.

In one aspect, the present invention relates to a process for the preparation of a compound of formula (I) as described herein, further comprising the reaction of a compound of formula (I) or salts thereof, in a solvent, such as DMF or THF, in the presence of CDI, together with a compound of formula (V), in a solvent, to give a compound of formula (VI), wherein $R^1$, $R^2$, $R^8$ and $R^9$ are as described herein.

In one aspect, the present invention relates to a process for the preparation of a compound of formula (I) as described herein, further comprising the reaction of a compound of formula (I) or salts or esters thereof, in a solvent, such as toluene, in the presence of $Me_3Al$, together with a compound of formula (V), in a solvent, such as dioxane, to give a compound of formula (VI), wherein $R^1$, $R^2$, $R^8$ and $R^9$ are as described herein.

In one aspect, the present invention relates to a process for the preparation of a compound of formula (I) as described herein, further comprising the reaction of a compound of formula (I) or salts or esters thereof, in a solvent, such as toluene, in the presence of TBD, together with a compound of formula (V), to give a compound of formula (VI), wherein $R^1$, $R^2$, $R^8$ and $R^9$ are as described herein.

In one aspect, the present invention relates to a process for the preparation of a compound of formula (I) as described herein, further comprising the reaction of a compound of formula (I) or salts thereof, in a solvent, such as THF, in the presence of CDI, with or without DMAP, and a base such as triethylamine (TEA), together with a compound of formula (V), to give a compound of formula (VI), wherein $R^1$, $R^2$, $R^8$ and $R^9$ are as described herein.

In one aspect, the present invention relates to a process for the preparation of a compound of formula (I) as described herein, further comprising:
i) the reaction of a compound of formula (I) or salts thereof, in a solvent, such as DMF, in the presence of TBTU and DIPEA, together with a compound of formula (V), in a solvent, such as methanol, to give a compound of formula (VI); or
ii) the reaction of a compound of formula (I) or salts thereof, in a solvent, such as THF, in the presence of HOBT, DIPEA and EDAC, together with a compound of formula (V), to give a compound of formula (VI); or
iii) the reaction of a compound of formula (I) or salts thereof, in a solvent, such as DMF or THF, in the presence of CDI, together with a compound of formula (V), in a solvent, to give a compound of formula (VI); or
iv) the reaction of a compound of formula (I) or salts or esters thereof, in a solvent, such as toluene, in the presence of $Me_3Al$, together with a compound of formula (V), in a solvent, such as dioxane, to give a compound of formula (VI); or
v) the reaction of a compound of formula (I) or salts or esters thereof, in a solvent, such as toluene, in the presence of TBD, together with a compound of formula (V), to give a compound of formula (VI); or
vi) the reaction of a compound of formula (I) or salts thereof, in a solvent, such as THF, in the presence of CDI, with or without DMAP, and a base such as triethylamine (TEA), together with a compound of formula (V), to give a compound of formula (VI);

In one aspect, the present invention relates to a process for the preparation of a compound of formula (I) as described herein, further comprising the reaction of a compound of formula (I) or salts thereof with a compound of formula (V) to give a compound of formula (VI) as described herein, wherein $R^1$, $R^2$, $R^8$ and $R^9$ are as described herein, wherein the compound of formula (V) is employed in a salt form, in particularly as a hydrochloric salt, which is converted to the free base of the compound of formula (V) by reaction with lithium tert-butoxide (LiOtBu), in a solvent, such as THF or a mixture of THF with a polar solvent such as DMF or DMSO, prior to reaction with a compound of formula (I).

In one aspect of the present invention, $R^8$ is alkyl, haloalkyl, hydroxyalkyl, cycloalkyl, cycloalkylalkyl, heterocycloalkyl, heterocycloalkylalkyl, aryl, heteroaryl, or heteroarylalkyl, wherein heterocycloalkyl, aryl and heteroaryl are optionally substituted with one halogen or alkyl.

In one aspect of the present invention, $R^8$ is isopropyl, trifluoroethyl, hydroxypropyl, cyclopropyl, cyclopropylmethyl, tetrahydropyranyl, isoxazolylmethyl substituted by isopropyl, phenyl substituted by fluoro, pyrazolyl substituted by methyl, or pyridinylmethyl.

In one aspect of the present invention, $R^8$ is isopropyl, trifluoroethyl, hydroxypropyl, cyclopropyl, cyclopropylmethyl, tetrahydropyranyl, isoxazolylmethyl substituted by isopropyl, phenyl substituted by fluoro, pyrazolyl substituted by methyl, or pyridinylmethyl.

In one aspect of the present invention, $R^8$ is isopropyl, trifluoroethyl, cyclopropylmethyl, or tetrahydropyranyl.

In one aspect of the present invention, $R^9$ is hydrogen or alkyl.

In one aspect of the present invention, $R^9$ is hydrogen or methyl.

In one aspect of the present invention, $R^9$ is hydrogen.

In one aspect of the present invention, $R^8$ and $R^9$ together with the nitrogen to which they are attached to form a heterocycloalkyl or heteroaryl, wherein heterocycloalkyl is optionally substituted with one or more hydroxy, or oxo.

In one aspect of the present invention, $R^8$ and $R^9$ together with the nitrogen to which they are attached to form thiazolidinyl, piperidinyl substituted by hydroxy, morpholinyl, thiomorpholinyl, 1,1-dioxo-thiomorpholin-4-yl, or 5,6-Dihydro-8H-[1,2,4]triazolo[4,3-a]pyrazin-7-yl.

In one aspect of the present invention, $R^8$ and $R^9$ together with the nitrogen to which they are attached to form morpholinyl, or 1,1-dioxo-thiomorpholin-4-yl.

In one aspect of the present invention, the compound of formula (V) is thiomorpholine-1,1-dioxide or thiomorpholine-1,1-dioxide HCl.

In one aspect, the present invention relates to a process for the preparation of a compound of formula (I) as described herein, further comprising the reaction of a compound of formula (I) or salts or esters thereof with a compound of formula (V) to a compound of formula (VI) selected from the group consisting of:
N-Methyl-6-(5-methyl-3-phenyl-isoxazol-4-ylmethoxy)-N-(tetrahydro-pyran-4-yl)-nicotinamide;
N-(4-Fluoro-phenyl)-6-(5-methyl-3-phenyl-isoxazol-4-ylmethoxy)-nicotinamide;
6-(5-Methyl-3-phenyl-isoxazol-4-ylmethoxy)-N-(1-methyl-1H-pyrazol-4-yl)-nicotinamide;
N-(3-Isopropyl-isoxazol-5-ylmethyl)-6-(5-methyl-3-phenyl-isoxazol-4-ylmethoxy)-nicotinamide;
6-(5-Methyl-3-phenyl-isoxazol-4-ylmethoxy)-N-pyridin-2-ylmethyl-nicotinamide;
[6-(5-Methyl-3-phenyl-isoxazol-4-ylmethoxy)-pyridin-3-yl]-thiazolidin-3-yl-methanone;
(4-Hydroxy-piperidin-1-yl)-[6-(5-methyl-3-phenyl-isoxazol-4-ylmethoxy)-pyridin-3-yl]-methanone;
(5,6-Dihydro-8H-[1,2,4]triazolo[4,3-a]pyrazin-7-yl)-[6-(5-methyl-3-phenyl-isoxazol-4-ylmethoxy)-pyridin-3-yl]-methanone;
6-[3-(3-Fluoro-phenyl)-5-methyl-isoxazol-4-ylmethoxy]-N-(2,2,2-trifluoro-ethyl)-nicotinamide;
{6-[3-(3-Fluoro-phenyl)-5-methyl-isoxazol-4-ylmethoxy]-pyridin-3-yl}-thiomorpholin-4-yl-methanone;
N-Cyclopropyl-6-[3-(3-fluoro-phenyl)-5-methyl-isoxazol-4-ylmethoxy]-nicotinamide;
{6-[3-(3-Chloro-phenyl)-5-methyl-isoxazol-4-ylmethoxy]-pyridin-3-yl}-(1,1-dioxo-1$\lambda^6$-thiomorpholin-4-yl)-methanone;
6-[3-(4-Fluoro-phenyl)-5-methyl-isoxazol-4-ylmethoxy]-N-(tetrahydro-pyran-4-yl)-nicotinamide;

(1,1-dioxo-1λ⁶-thiomorpholin-4-yl)-{6-[3-(4-fluoro-phenyl)-5-methyl-isoxazol-4-ylmethoxy]-pyridin-3-yl}-methanone;
6-[3-(4-Fluoro-phenyl)-5-methyl-isoxazol-4-ylmethoxy]-N-isopropyl-nicotinamide;
N-Cyclopropylmethyl-6-[3-(4-fluoro-phenyl)-5-methyl-isoxazol-4-ylmethoxy]-nicotinamide;
{6-[3-(4-Fluoro-phenyl)-5-methyl-isoxazol-4-ylmethoxy]-pyridin-3-yl}-morpholin-4-yl-methanone;
6-[3-(4-Fluoro-phenyl)-5-methyl-isoxazol-4-ylmethoxy]-N-(2,2,2-trifluoro-ethyl)-nicotinamide;
6-[3-(4-Chloro-phenyl)-isoxazol-4-ylmethoxy]-N-isopropyl-nicotinamide;
6-[3-(4-Chloro-phenyl)-isoxazol-4-ylmethoxy]-N-(3-hydroxy-propyl)-nicotinamide;
6-[3-(4-Chloro-phenyl)-5-methyl-isoxazol-4-ylmethoxy]-N-cyclopropylmethyl-nicotinamide;
and 6-[3-(4-Chloro-phenyl)-5-methyl-isoxazol-4-ylmethoxy]-N-(1-methyl-1H-pyrazol-4-yl)-nicotinamide;
and pharmaceutically acceptable salts thereof.

In one aspect, the present invention relates to a process for the preparation of a compound of formula (I) as described herein, further comprising the reaction of a compound of formula (I) or salts or esters thereof with a compound of formula (V) to a compound of formula (VI) selected from the group consisting of:
6-[3-(4-Fluoro-phenyl)-5-methyl-isoxazol-4-ylmethoxy]-N-(tetrahydro-pyran-4-yl)-nicotinamide;
(1,1-dioxo-1λ⁶-thiomorpholin-4-yl)-{6-[3-(4-fluoro-phenyl)-5-methyl-isoxazol-4-ylmethoxy]-pyridin-3-yl}-methanone;
6-[3-(4-Fluoro-phenyl)-5-methyl-isoxazol-4-ylmethoxy]-N-isopropyl-nicotinamide;
N-Cyclopropylmethyl-6-[3-(4-fluoro-phenyl)-5-methyl-isoxazol-4-ylmethoxy]-nicotinamide;
{6-[3-(4-Fluoro-phenyl)-5-methyl-isoxazol-4-ylmethoxy]-pyridin-3-yl}-morpholin-4-yl-methanone; and
6-[3-(4-Fluoro-phenyl)-5-methyl-isoxazol-4-ylmethoxy]-N-(2,2,2-trifluoro-ethyl)-nicotinamide;
and pharmaceutically acceptable salts thereof.

In one aspect, the present invention relates to a process for the preparation of a compound of formula (I) as described herein, further comprising the reaction of a compound of formula (I) or salts or esters thereof with a compound of formula (V) to 6-[3-(4-Fluoro-phenyl)-5-methyl-isoxazol-4-ylmethoxy]-N-(tetrahydro-pyran-4-yl)-nicotinamide or pharmaceutically acceptable salts thereof.

In one aspect, the present invention relates to a process for the preparation of a compound of formula (I) as described herein, further comprising the reaction of a compound of formula (I) or salts or esters thereof with a compound of formula (V) to (1,1-dioxo-1λ⁶-thiomorpholin-4-yl)-{6-[3-(4-fluoro-phenyl)-5-methyl-isoxazol-4-ylmethoxy]-pyridin-3-yl}-methanone or pharmaceutically acceptable salts thereof.

In one aspect, the present invention relates to a process for the preparation of a compound of formula (I) as described herein, further comprising the reaction of a compound of formula (I) or salts or esters thereof with a compound of formula (V) 6-[3-(4-Fluoro-phenyl)-5-methyl-isoxazol-4-ylmethoxy]-N-isopropyl-nicotinamide or pharmaceutically acceptable salts thereof.

In one aspect, the present invention relates to a process for the preparation of a compound of formula (I) as described herein, further comprising the reaction of a compound of formula (I) or salts or esters thereof with a compound of formula (V) to N-Cyclopropylmethyl-6-[3-(4-fluoro-phenyl)-5-methyl-isoxazol-4-ylmethoxy]-nicotinamide or pharmaceutically acceptable salts thereof.

In one aspect, the present invention relates to a process for the preparation of a compound of formula (I) as described herein, further comprising the reaction of a compound of formula (I) or salts or esters thereof with a compound of formula (V) to {6-[3-(4-Fluoro-phenyl)-5-methyl-isoxazol-4-ylmethoxy]-pyridin-3-yl}-morpholin-4-yl-methanone or pharmaceutically acceptable salts thereof.

In one aspect, the present invention relates to a process for the preparation of a compound of formula (I) as described herein, further comprising the reaction of a compound of formula (I) or salts or esters thereof with a compound of formula (V) to 6-[3-(4-Fluoro-phenyl)-5-methyl-isoxazol-4-ylmethoxy]-N-(2,2,2-trifluoro-ethyl)-nicotinamide or pharmaceutically acceptable salts thereof.

In one aspect, the present invention relates to a process for the preparation of a compound of formula (VI) as described herein, comprising the reaction of a compound of formula (II) with a compound of formula (III) to a compound of formula (IV),
followed by the reaction of the compound of formula (IV) to a compound of formula (I),
followed by the reaction of the compound of formula (I) with a compound of formula (V) to a compound of formula (VI);
wherein the compound of formula (II) is 3-(4-Fluoro-phenyl)-5-methyl-isoxazol-4-ylmethanol [CAS No. 1018297-63-6],
wherein the compound of formula (III) is 6-chloronicotinonitrile [CAS No. 33252-28-7],
wherein the compound of formula (IV) is 6-[3-(4-Fluoro-phenyl)-5-methyl-isoxazol-4-ylmethoxy]-nicotinonitrile,
wherein the compound of formula (I) is 6-[3-(4-Fluoro-phenyl)-5-methyl-isoxazol-4-ylmethoxy]-nicotinic acid [CAS No. 1159600-32-4] or salts thereof,
wherein the compound of formula (V) is thiomorpholine-1,1-dioxide [CAS No. 39093-93-1] or salts thereof,
wherein the compound of formula (VI) is (1,1-dioxo-1λ⁶-thiomorpholin-4-yl)-{6-[3-(4-fluoro-phenyl)-5-methyl-isoxazol-4-ylmethoxy]-pyridin-3-yl}-methanone [CAS No. 1159600-41-5] or pharmaceutically acceptable salts thereof.

In one aspect, the present invention relates to compounds obtainable by any process as described herein.

EXAMPLES

The following examples 1-34 are provided for illustration of the invention. They should not be considered as limiting the scope of the invention, but merely as being representative thereof.

Example 1

(5-Methyl-3-phenyl-isoxazol-4-yl)]-methanol

The title compound was purchased from ABCR GmbH KG, Karlsruhe, Germany

Example 2

3-(3-Fluoro-phenyl)-5-methyl-isoxazol-4-ylmethanol

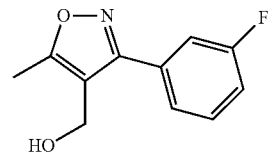

Step a) (E)- and/or (Z)-3-Fluoro-benzaldehyde oxime

To a suspension of 3-fluorobenzaldehyde (6.75 g, 54 mmol) and hydroxylamine hydrochloride (4.16 g, 60 mmol) in ethanol (4.3 mL) and water (13 mL) was added ice (25 g). Then a solution of sodium hydroxide (5.5 g, 138 mmol) in water (6.5 mL) was added dropwise within a 10 min period (temperature rises from −8° C. to +7° C.) whereupon most of the solid dissolves. After 30 min stirring at room temperature a white solid precipitated and the resulting mixture was then diluted with water and acidified with HCl (4 N). The white precipitate was then filtered off, washed with water and dried under high vacuum to afford the title compound (7.0 g, 93%) which was obtained as a white solid. MS m/e (EI): 139.1 [M].

Step b) (E)- and/or (Z)—N-Hydroxy-3-fluoro-benzenecarboximidoyl chloride

To a solution of (E)- and/or (Z)-3-fluoro-benzaldehyde oxime (6.9 g, 50 mmol) in DMF (50 mL) was added N-chlorosuccinimide (6.6 g, 50 mmol) portionwise over 1 h, keeping the temperature below 35° C. The reaction mixture was stirred at room temperature for 1 h. The mixture was then poured onto ice-water, and extracted with ethyl acetate. The combined organic layers were then washed with water and brine, dried over sodium sulfate and evaporated to afford the title compound (6.3 g, 73%) which was obtained as an off white solid. MS m/e (EI): 173.1 [M].

Step c) 3-(3-Fluoro-phenyl)-5-methyl-isoxazole-4-carboxylic acid ethyl ester To a solution of (E)- and/or (Z)—N-hydroxy-3-fluoro-benzenecarboximidoyl chloride (11.1 g, 64 mmol) in diethylether (151 mL) was added ethyl 2-butynoate (7.2 g, 7.5 mL, 64 mmol) at 0° C. followed by the dropwise addition of triethylamine (7.8 g, 10.7 mL, 77 mmol) and the resulting mixture allowed to warm up to room temperature overnight. The mixture was then poured onto ice-water, and extracted with diethylether. The combined organic layers were then washed with water and brine, dried over sodium sulfate and evaporated. Purification by chromatography (SiO$_2$, heptane:ethyl acetate=100:0 to 1:1) afforded the title compound (6.3 g, 39%) which was obtained as a white solid. MS: m/e=250.1 [M+H]$^+$.

Step d) [3-(3-Fluoro-phenyl)-5-methyl-isoxazol-4-yl]-methanol

To a solution of 3-(3-fluoro-phenyl)-5-methyl-isoxazole-4-carboxylic acid ethyl ester (6.18 g, 25 mmol) in THF (320 mL) was added portionwise lithiumaluminiumhydride (528 mg, 14 mmol) at 0° C. and the reaction mixture was stirred at room temperature for 3 h. The mixture was then cooled to 0° C. and water (518 µL) added followed by sodium hydroxide (15% solution, 518 µL) and then again water (1.5 mL) and the mixture then stirred overnight at room temperature. The precipitate was then filtered off and washed with THF. The combined washings and filtrate were then evaporated. Purification by chromatography (SiO2, heptane:ethyl acetate=100:0 to 1:1) afforded the title compound (3.9 g, 75%) which was obtained as a yellow solid. MS: m/e=208.3 [M+H]$^+$.

Example 3

3-(3-Chloro-phenyl)-5-methyl-isoxazol-4-ylmethanol

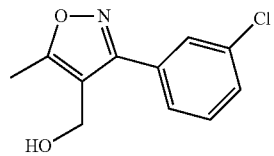

Step a) (E)- and/or (Z)-3-Chloro-benzaldehyde oxime

To a suspension of 3-chlorobenzaldehyde (50 g, 355 mmol) and hydroxylamine hydrochloride (38 g, 543 mmol) in ethanol (200 mL) containing sodium acetate (46 g, 558 mmol) was heated under reflux for 3 h. After 30 min stirring at room temperature a white solid precipitated and the resulting mixture was then diluted with water and acidified with HCl (4 N). The white precipitate was then filtered off, washed with water and dried under high vacuum to afford the title compound (54 g, 98%) which was obtained as a white solid. Mp: 64-66° C.

Step b) (E)- and/or (Z)—N-Hydroxy-3-chloro-benzenecarboximidoyl chloride

To a solution of (E)- and/or (Z)-3-chloro-benzaldehyde oxime (54 g, 347 mmol) in DMF (800 mL) was added HCl (conc., 17 mL) and the mixture cooled to room temperature. Then potassium monopersulfate triple salt (247 g, 400 mmol) and the reaction mixture was stirred at room temperature for 1 h. The mixture was then poured onto ice-water, and extracted with ethyl acetate. The combined organic layers were then washed with water and brine, dried over sodium sulfate and evaporated to afford the title compound (66 g, 100%) which was obtained as a white solid. Mp: 58-60° C.

Step c) 3-(3-Chloro-phenyl)-5-methyl-isoxazole-4-carboxylic acid ethyl ester To a suspension of sodium (2.67 g, 116 mmol) in methanol (100 mL) was added ethyl acetoacetate (12.8 g, 11.9 mL, 110 mmol) at room temperature over 15 minutes and then a solution of (E)- and/or (Z)—N-hydroxy-3-chloro-benzenecarboximidoyl chloride (19.0 g, 100 mmol) in methanol (100 mL) was added over 20 minutes and the resulting mixture allowed to stir for 4 h at room temperature. The mixture was then poured onto water and cooled to 5° C., filtered and evaporated. Purification by recrystallisation from ethanol afforded the title compound (10.1 g, 40%) which was obtained as a white solid. Mp: 71-73° C.

Step d) 3-(3-Chloro-phenyl)-5-methyl-isoxazole-4-carboxylic acid

To a solution of 3-(3-chloro-phenyl)-5-methyl-isoxazole-4-carboxylic acid ethyl ester (9.1 g, 36 mmol) in ethanol (50 mL) was added aqueous sodium hydroxide (4 N, 10 mL). After heating at reflux for 1 h the mixture was cooled to room temperature and acidified with HCl (4 N, 10 mL) and water (10 mL) at 0° C. Purification by filtration and drying afforded the title compound (8.3 g, 97%) which was obtained as a white solid. Mp: 171-173° C.

Step e) [3-(3-Chloro-phenyl)-5-methyl-isoxazol-4-yl]-methanol

To a solution of 3-(3-chloro-phenyl)-5-methyl-isoxazole-4-carboxylic acid (4.8 g, 20 mmol in THF (50 mL) at −10° C. was added triethylamine (2.9 mL, 21 mmol) and then a solution of ethylchloroformate (1.96 mL, 20 mmol) in THF (10 mL) added keeping the temperature below −5° C. After 1 h the mixture was filtered and the filtrate cooled to −10° C. and a suspension of sodiumborohydride (2.0 g, 50 mmol) in water (10 mL) added over 15 minutes keeping the temperature below −5° C. The mixture was then allowed to warm up to room temperature over 2 h and diluted with sodium hydroxide (2 N, 30 mL) and extracted with ethyl acetate. The combined organic layers were then washed with water and brine, dried over sodium sulfate and evaporated to afford the title compound (3.5 g, 78%) which was obtained as a clear oil which solidified with time as a white solid. Mp: 66-68° C.

Example 4

3-(4-Fluoro-phenyl)-5-methyl-isoxazol-4-ylmethanol

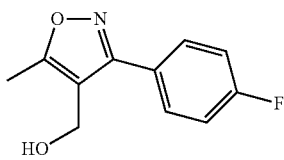

Step a) (E)- and/or (Z)-4-fluoro-benzaldehyde oxime

To a suspension of 4-fluoro-benzaldehyde (30.4 g, 0.24 mol) in water (50 mL) was added at 0-5° C. within 5 minutes a solution of hydroxylamine hydrochloride (17.7 g, 0.25 mol) in water (30 mL) and the resulting mixture stirred for 15 minutes at 0-5° C. The mixture was then treated at 15-25° C. within 15 minutes with 32% NaOH (24.44 mL, 0.26 mol) and the resulting suspension was stirred for one additional hour and then extracted with ethyl acetate (3×100 mL). The combined organic layers were washed with water (2×100 mL) and subsequently concentrated to dryness to afford 31.9 g (95%) of the title compound as a white solid.

Step b) 3-(4-Fluoro-phenyl)-5-methyl-isoxazole-4-carboxylic acid ethyl ester To a suspension of 4-fluoro-benzaldehyde oxime (1.39 g, 10.0 mmol) in DMF (10 mL) was added portionwise within 5 minutes at 15 to 20° C. N-chlorosuccinimide (1.36 g, 10.0 mmol) and the resulting mixture was stirred at room temperature for 90 minutes. The yellow solution (containing N-Hydroxy-4-fluoro-benzenecarboximidoyl chloride) was then treated within 2 minutes at room temperature with a solution of ethyl-3-(1-pyrrolidino)crotonate (1.89 g, 10.0 mmol) in 5 mL of DMF and the resulting solution was stirred at room temperature for 28 hours. The mixture was diluted with water (25 mL) and subsequently extracted with ethyl acetate (4×25 mL). The combined organic layers were washed with 1 M HCl (2×25 mL) and water (2×25 mL), dried over Na$_2$SO$_4$ and subsequently concentrated to dryness (45° C./25 mbar) to afford 2.37 g (95%) of the title compound as a brownish solid with a purity of 100% (by GC) and 97% (by HPLC).

Step c) 3-(4-Fluoro-phenyl)-5-methyl-isoxazole-4-carboxylic acid

A mixture of 179.5 g (0.72 mol) of 3-(4-Fluoro-phenyl)-5-methyl-isoxazole-4-carboxylic acid ethyl ester in 880 g of ethanol 95% was stirred at 20-30° C. for 40 minutes and then treated with 78.5 g of solid sodium hydroxide. The resulting mixture was stirred for 5 h at 20-30° C. Ethanol was removed in vacuum at 45-50° C. and the residue was subsequently treated with 500 g of water at 20-30° C. to afford a clear solution. The solution was stirred for 40 minutes and filtered. To the filtrate was added 235 g of methyl tert-butyl ether and 600 g of water and the resulting mixture stirred for 20 min and then stood for 20 min. The layers were separated and the aqueous layer was acidified to pH<1 with hydrochloric acid. The crystals were filtered and washed with water to provide 147 g crude wet product. The crude wet product was suspended in 680 g of toluene and the mixture was heated at 75-85° C. for 7 h. The mixture was cooled to 20-30° C. and stirred for 1 hour at this temperature. The crystals were filtered off and dried at 50-55° C. in vacuum over night to afford 137 g (86% yield) of the title acid as a white to slightly yellow solid with a purity of 99.9% (HPLC).

Step d) [3-(4-Fluorophenyl)-5-methyl-isoxazol-4-yl]-methanol

Alternative 1) Preparation by Reduction of the Acid

A suspension of 448 g of tetrahydrofuran and 95 g (0.70 mol) of zinc chloride was stirred at 20-30° C. for 1 h. 23.6 g (0.62 mol) of sodium borohydride were added in portions at 20-38° C. and the mixture subsequently stirred at 60-65° C. for 3 h. A solution of 69 g (0.31 mol) of 3-(4-Fluoro-phenyl)-5-methyl-isoxazole-4-carboxylic acid in 220 g THF was added dropwise and the resulting mixture stirred at 60-65° C. for 16 h. The reaction was then quenched by the drop wise addition of a mixture of 93 g of HCl in 202 g of water at 5-10° C. The mixture was stirred at this temperature for 2 h to dissolve the solids completely. The solvent was removed under reduced pressure with a jacket temperature of 35-40° C. To the residue were added 510 g of water. The resulting suspension was cooled to 20-30° C. and the crystals were filtered off and washed with water. The crude wet product was stirred for 1 h in a mixture of 150 g of water, 31 g of HCl and 419 g of MTBE. The lower aqueous phase was removed and the organic phase was dried with anhydrous sodium sulfate, stirred for 0.5 h and filtered under nitrogen. The filtrate was almost completely concentrated under reduced pressure at 40-45° C. The residue was treated at 20-25° C. with 100 g of MTBE. The mixture was stirred at 55-60° C. for 2 h, cooled to 0° C. and subsequently stirred at this temperature for additional 2 h. The crystals were filtered off and dried at 45-50° C. in vacuum over night to afford 42 g (66% yield) of the title alcohol as an off-white solid with a purity of 99.9% (HPLC).

Alternative 2) Preparation by Reduction of the Ethyl Ester (i) with LiAlH$_4$ as Reducing Agent:

To a suspension of LiAlH$_4$ (75.9 mg, 2.0 mmol) in THF (2 mL) was added at 0-10° C. within 15 minutes a solution of 3-(4-Fluoro-phenyl)-5-methyl-isoxazole-4-carboxylic acid ethyl ester (0.50 g, 2.0 mmol) in THF (3 mL) and the resulting solution was allowed to warm to room temperature and subsequently stirred at this temperature for at least one hour. Water (15 mL) was added dropwise and the resulting suspension was then filtered and the filter cake washed with ethyl acetate (15 mL). From the biphasic filtrate the layers were separated and the organic layer was washed with water (1×15 mL). Both combined aqueous layers were back extracted with ethyl acetate (2×15 mL). The combined organic layers were dried over Na$_2$SO$_4$ and subsequently concentrated to dryness (45° C./25 mbar) to afford 0.375 g (90%) of the title compound as a slightly yellow solid with a purity of 100% (by HPLC).

(ii) with Red-Al (Vitride) as Reducing Agent:

To a solution of sodium bis(2-methoxyethoxy)aluminumhydride (Red-Al; 3 M in toluene; 0.857 mL, 3.0 mmol; 1.5 eq.) in THF (2 mL) was added at 0-5° C. within 5 minutes a solution of 3-(4-Fluoro-phenyl)-5-methyl-isoxazole-4-carboxylic acid ethyl ester (0.513 g, 2.0 mmol) in THF (2 mL) and the resulting solution was allowed to warm to room temperature and subsequently stirred at this temperature for 5 h. Water (15 mL) was added dropwise and the resulting mixture was extracted with ethyl acetate (3×15 mL). The combined organic layers were washed with water (2×15 mL), dried over Na$_2$SO$_4$ and subsequently concentrated to dryness (45° C./25 mbar) to afford 0.395 g (95%) of the title compound as orange crystals with a purity of 92% (by HPLC).

Example 5

3-(4-Chloro-phenyl)-isoxazol-4-ylmethanol

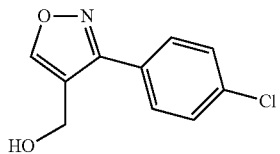 [SMILES: OCc1conc1-c1ccc(Cl)cc1]

Step a) (E)- and/or (Z)-4-Chloro-benzaldehyde oxime

To a suspension of 4-chlorobenzaldehyde (25.0 g, 178 mmol) and hydroxylamine hydrochloride (13.7 g, 198 mmol) in ethanol (14.1 mL) and water (42.9 mL) was added ice (82 g). Then a solution of sodium hydroxide (18.1 g, 454 mmol) in water (21.4 mL) was added dropwise within a 10 min period (temperature rises from −8° C. to +7° C.) whereupon most of the solid dissolves. After 30 min stirring at room temperature a white solid precipitated and the resulting mixture was then diluted with water and acidified with HCl (4 N). The white precipitate was then filtered off, washed with water and dried under high vacuum to afford the title compound (27.0 g, 97%) which was obtained as an off white solid. MS m/e (EI): 155.1 [M]$^+$.

Step b) (E)- and/or (Z)—N-Hydroxy-4-chloro-benzenecarboximidoyl chloride

To a solution of (E)- and/or (Z)-4-chloro-benzaldehyde oxime (27.0 g, 173 mmol) in DMF (173 mL) was added N-chlorosuccinimide (22.8 g, 173 mmol) portionwise over 1 h, keeping the temperature below 35° C. The reaction mixture was stirred at room temperature for 1 h. The mixture was then poured onto ice-water, and extracted with ethyl acetate. The combined organic layers were then washed with water and brine, dried over sodium sulfate and evaporated to afford the title compound (28.4 g, 86%) which was obtained as a light yellow solid. MS: m/e=189.1 [M]$^+$.

Step c) 3-(4-Chloro-phenyl)-isoxazole-4-carboxylic acid ethyl ester

To a solution of (E)- and/or (Z)—N-hydroxy-4-chloro-benzenecarboximidoyl chloride (58.0 g, 250.3 mmol) in diethylether (1.04 L) was added a solution of ethyl 3-(N,N-dimethylamino)acrylate (90.4 mL, 624 mmol) and triethylamine (50.1 mL, 362 mmol) in diethylether (1.04 L). The resulting mixture was then stirred for 14 h at room temperature and evaporated. Purification by chromatography (SiO$_2$, heptane:ethyl acetate=100:0 to 4:1) afforded the title product (57 g, 91%) which was obtained as a white solid. MS: m/e=252.1 [M+H]$^+$.

Step d) 3-(4-Chloro-phenyl)-isoxazole-4-carboxylic acid

To a solution of 3-(4-chloro-phenyl)-isoxazole-4-carboxylic acid ethyl ester (57.0 g, 226.5 mmol) in ethanol (234 mL) was added aqueous sodium hydroxide (2 N, 175 mL, 351 mmol) and the resulting mixture stirred overnight at room temperature. The mixture was then acidified with HCl solution (4 N, 92.6 mL) to pH 2-3. The precipitate was then filtered off and dissolved in THF (762 mL) and then washed with saturated sodium chloride solution. The aqueous phase was then extracted with ethyl acetate and THF (1:1, 300 mL) and the combined organic phases dried over sodium sulfate and evaporated to afford the title compound (50.7 g, 92%) which was obtained as a light yellow solid. MS: m/e=222.3 [M−H]$^−$.

Step e) [3-(4-Chloro-phenyl)-isoxazol-4-yl]-methanol

To a solution of 3-(4-chloro-phenyl)-isoxazole-4-carboxylic acid (40.0 g, 178.9 mmol) in THF (370 mL) at −10° C. was added triethylamine (25.1 mL, 179 mmol) and then a solution of ethylchloroformate (17.4 mL, 179 mmol) in THF (111 mL) added keeping the temperature below −5° C. After 1 h the mixture was filtered and the filtrate cooled to −10° C. and a suspension of sodiumborohydride (17.6 g, 447 mmol) in water (111 mL) added over 15 minutes keeping the temperature below −5° C. The mixture was then allowed to warm up to room temperature over 2 h and diluted with aqueous sodium hydroxide (1 N, 648 mL) and extracted with tert-butylmethylether. The combined organic layers were then washed with water and brine, dried over sodium sulfate and evaporated. Purification by chromatography (SiO2, heptane:ethyl acetate=1:1) afforded the title product (17.3 g, 46%) which was obtained as a light green solid. MS: m/e=210.1 [M+H]$^+$.

Example 6

3-(4-Chloro-phenyl)-5-methyl-isoxazol-4-ylmethanol

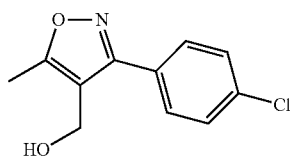

Step a) (E)- and/or (Z)-4-Chloro-benzaldehyde oxime

To a suspension of 4-chlorobenzaldehyde (25.0 g, 178 mmol) and hydroxylamine hydrochloride (13.7 g, 198 mmol) in ethanol (14.2 mL) and water (42.9 mL) was added ice (82.4 g). Then a solution of sodium hydroxide (18.1 g, 455 mmol) in water (21.4 mL) was added dropwise within a 10 min period (temperature rises from −8° C. to +7° C.) whereupon most of the solid dissolves. After 30 min stirring at room temperature a white solid precipitated and the resulting mixture was then diluted with water and acidified with HCl (4 N).

The white precipitate was then filtered off, washed with water and dried under high vacuum to afford the title compound (27.0 g, 97%) which was obtained as an off white solid. MS: m/e=155.1 [M]+.

Step b) (E)- and/or (Z)—N-Hydroxy-4-chloro-benzenecarboximidoyl chloride

To a solution of (E)- and/or (Z)-4-chloro-benzaldehyde oxime 4-fluorobenzaldehyde (27.0 g, 173 mmol) in DMF (173 mL) was added N-chlorosuccinimide (22.8 g, 173 mmol) portionwise over 1 h, keeping the temperature below 35° C. The reaction mixture was stirred at room temperature for 1 h. The mixture was then poured onto ice-water, and extracted with ethyl acetate. The combined organic layers were then washed with water and brine, dried over sodium sulfate and evaporated to afford the title compound (28.4 g, 86%) which was obtained as a light yellow solid. MS: m/e=189.1 [M]+.

Step c) 3-(4-Chloro-phenyl)-5-methyl-isoxazole-4-carboxylic acid ethyl ester

To a solution of (E)- and/or (Z)—N-hydroxy-4-chloro-benzenecarboximidoyl chloride (26.0 g, 137 mmol) in diethylether (323 mL) was added ethyl 2-butynoate (15.4 g, 16.1 mL, 137 mmol) at 0° C. followed by the dropwise addition of triethylamine (24.1 g, 22.9 mL, 164 mmol) and the resulting mixture allowed to warm up to room temperature overnight. The mixture was then poured onto ice-water, and extracted with diethylether. The combined organic layers were then washed with water and brine, dried over sodium sulfate and evaporated. Purification by chromatography (SiO$_2$, heptane:ethyl acetate=100:0 to 1:1) afforded the title compound (15.2 g, 42%) which was obtained as a light yellow solid. MS: m/e=266.1 [M+H]+.

Step d) [3-(4-Chloro-phenyl)-5-methyl-isoxazol-4-yl]-methanol

To a solution of 3-(4-chloro-phenyl)-5-methyl-isoxazole-4-carboxylic acid ethyl ester (373 mg, 1.4 mmol) in THF (17.9 mL) was added portionwise lithiumaluminiumhydride (29.6 mg, 0.78 mmol) at 0° C. and the reaction mixture was stirred at room temperature for 3 h. The mixture was then cooled to 0° C. and water (29.0 µL) added followed by sodium hydroxide (15% solution, 29.0 µL) and then again water (84.0 µL) and the mixture then stirred overnight at room temperature. The precipitate was then filtered off and washed with THF. The combined washings and filtrate were then evaporated. Purification by chromatography (SiO$_2$, heptane:ethyl acetate=100:0 to 1:1) afforded the title compound (204 mg, 65%) which was obtained as a white solid. MS: m/e=224.1 [M+H]+.

Example 7

6-(5-Methyl-3-phenyl-isoxazol-4-ylmethoxy)-nicotinic acid

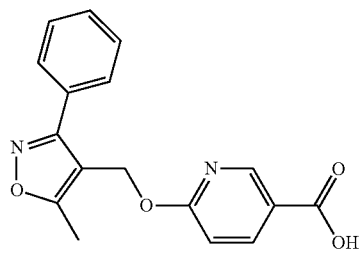 [SMILES: Cc1onc(-c2ccccc2)c1COc1ccc(C(=O)O)cn1]

To a solution of (5-methyl-3-phenyl-isoxazol-4-yl)-methanol (200 mg, 1.06 mmol) was added sodium hydride (55% dispersion in mineral oil, 996 mg, 22.8 mmol). After stirring for 0.5 h at ambient temperature methyl 6-chloronicotinate (1.06 mmol) was added and the reaction mixture was stirred for 5 h at ambient temperature. It was diluted with ethyl acetate (10 mL), washed with aqueous citric acid (10%, 10 mL), water (10 mL) and aqueous sodium chloride (saturated, 10 mL). The combined aqueous layers were extracted with ethyl acetate (10 mL). After drying over sodium sulfate and concentration purification by chromatography (SiO$_2$, heptane:ethyl acetate=100:0 to 70:30) afforded 6-(5-methyl-3-phenyl-isoxazol-4-ylmethoxy)-nicotinic acid methyl ester (191 mg, 42%) as a white solid. To a solution of 6-(5-methyl-3-phenyl-isoxazol-4-ylmethoxy)-nicotinic acid methyl ester (3.89 g, 120 mmol) in ethanol (40 mL) was added aqueous sodium hydroxide (1 M, 36.0 mL, 36.0 mmol). After heating at reflux for 2 h it was cooled to ambient temperature and concentrated. Addition of aqueous sodium hydroxide (1 M, 50 mL) was followed by washing with tert-butylmethylether (100 mL). The aqueous phase was acidified with aqueous hydrogen chloride (conc.) to pH=1 and extracted with tert-butylmethylether (100 mL). The organic layer was washed with water (50 mL) and aqueous sodium chloride (saturated, 50 mL). Drying over sodium sulfate and concentration afforded the title compound (1.68 g, 45%) as an off white solid. MS: m/e=309.3 [M−H]−.

Example 8

6-[3-(3-Fluoro-phenyl)-5-methyl-isoxazol-4-ylmethoxy]-nicotinic acid

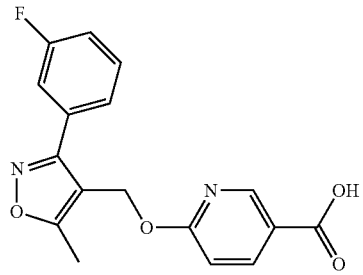 [SMILES: Cc1onc(-c2cccc(F)c2)c1COc1ccc(C(=O)O)cn1]

To a suspension of sodium hydride (55% dispersion in mineral oil, 852 mg, 20 mmol) in THF (27 mL) was added a solution of [3-(3-fluoro-phenyl)-5-methyl-isoxazol-4-yl]-methanol (3.68 g, 18 mmol) in THF (54 mL) at 0° C. and the reaction mixture warmed to room temperature over 30 min. Then a solution of methyl 6-chloronicotinate (3.35 g, 20 mmol) in THF (1.5 mL) was added dropwise at 0° C. and the reaction mixture was stirred at room temperature overnight. The reaction mixture was then poured into aqueous sodium chloride (saturated) and the mixture was extracted with ethyl acetate. The combined organic layers were then washed with water and brine and then dried over sodium sulfate, filtered and evaporated. Purification by chromatography (SiO2, heptane:ethyl acetate=7:3) afforded 6-[3-(3-fluoro-phenyl)-5-methyl-isoxazol-4-ylmethoxy]-nicotinic acid methyl ester (4.1 g, 68%) which was obtained as a white solid. To a solution of 6-[3-(3-fluoro-phenyl)-5-methyl-isoxazol-4-yl-methoxy]-nicotinic acid methyl ester (1.1 mmol) in THF (5 mL) was added a solution of lithium hydroxide monohydrate (94 mg, 2.2 mmol) in water (5 mL) and methanol (1 mL) added and the resulting mixture stirred at room temperature overnight. The mixture was acidified to pH 4 with HCl (25%, 3 drops) and methanol (2 drops) added. A gum began to form and the mixture was cooled at 0° C. for 1.5 h and then the aqueous layer decanted off. Trituration with diethylether and hexane afforded the title compound (95%) which was obtained as an off white solid. MS: m/e=327.4 [M−H]−.

Example 9

6-[3-(3-Chloro-phenyl)-5-methyl-isoxazol-4-yl-methoxy]-nicotinic acid

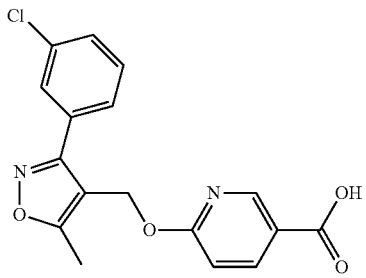 [SMILES: Cc1onc(-c2cccc(Cl)c2)c1COc1ccc(C(=O)O)cn1]

To a suspension of sodium hydride (55% dispersion in mineral oil, 852 mg, 20 mmol) in THF (27 mL) was added a solution of [3-(3-chloro-phenyl)-5-methyl-isoxazol-4-yl]-methanol (18 mmol) in THF (54 mL) at 0° C. and the reaction mixture warmed to room temperature over 30 min. Then a solution of methyl 6-chloronicotinate (3.35 g, 20 mmol) in THF (1.5 mL) was added dropwise at 0° C. and the reaction mixture was stirred at room temperature overnight. The reaction mixture was then poured into aqueous sodium chloride (saturated) and the mixture was extracted with ethyl acetate. The combined organic layers were then washed with water and brine and then dried over sodium sulfate, filtered and evaporated. Purification by chromatography ($SiO_2$, heptane: ethyl acetate=7:3) afforded 6-[3-(3-chloro-phenyl)-5-methyl-isoxazol-4-ylmethoxy]-nicotinic acid methyl ester (52%) which was obtained as an off-white solid. MS: m/e=359.4 $[M+H]^+$. To a solution of 6-[3-(3-chloro-phenyl)-5-methyl-isoxazol-4-ylmethoxy]-nicotinic acid methyl ester (1.1 mmol) in THF (5 mL) was added a solution of lithium hydroxide monohydrate (94 mg, 2.2 mmol) in water (5 mL) and methanol (1 mL) added and the resulting mixture stirred at room temperature overnight. The mixture was acidified to pH 4 with HCl (25%, 3 drops) and methanol (2 drops) added. A gum began to form and the mixture was cooled at 0° C. for 1.5 h and then the aqueous layer decanted off. Trituration with diethylether and hexane afforded the title compound (84%) which was obtained as a white solid. MS: m/e=343.4 $[M–H]^–$.

Example 10

6-[3-(4-Fluoro-phenyl)-5-methyl-isoxazol-4-yl-methoxy]-nicotinic acid

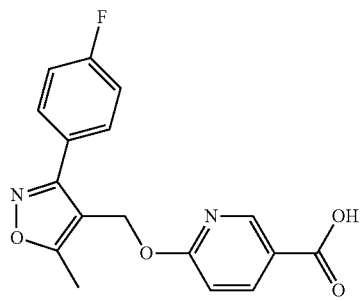 [SMILES: Cc1onc(-c2ccc(F)cc2)c1COc1ccc(C(=O)O)cn1]

Alternative 1

Two-Step Process

Step 1) 6-[3-(4-Fluoro-phenyl)-5-methyl-isoxazol-4-ylmethoxy]-nicotinonitrile

To a suspension of sodium hydride (60% in mineral oil, 7.9 g, 181 mmol, 1.5 eq.) in THF (65 mL) was added within 30 minutes at room temperature a solution of [3-(4-Fluorophenyl)-5-methyl-isoxazol-4-yl]-methanol (25.0 g, 121 mmol) and 6-chloronicotinonitrile (16.7 g, 121 mmol) in THF (120 mL) and the resulting mixture was stirred for one hour. A solution of citric acid (18.5 g, 96.5 mmol) in water (185 mL) was added to the reaction mixture within 30 minutes. From the resulting THF/water mixture THF was distilled off under reduced pressure at a jacket temperature of 60° C. and replaced by ethanol. In total 284 g of ethanol were added. The resulting suspension was stirred for one hour at room temperature. The crystals were filtered off, washed with a mixture of ethanol (60 mL) and water (60 mL) and subsequently dried at 50° C./<25 mbar to afford 36.5 g (91% corrected yield) of the title nitrile as an off-white solid with an assay of 93% (w/w).

Step 2) 6-[3-(4-Fluoro-phenyl)-5-methyl-isoxazol-4-ylmethoxy]-nicotinic acid

6-[3-(4-Fluoro-phenyl)-5-methyl-isoxazol-4-ylmethoxy]-nicotinonitrile (58.8 g, 190 mmol) was suspended in water (440 mL) and ethanol (600 mL) and treated with 32% sodium hydroxide solution (178 mL 1.92 mol). The mixture was heated to 50-55° C. and subsequently stirred at this temperature for 15 hour. The slightly turbid mixture was polish filtered to remove the ether by-product 6-[3-(4-Fluoro-phenyl)-5-methyl-isoxazol-4-ylmethoxymethyl-3-(4-fluoro-phenyl)-5-methyl-isoxazole. The first vessel and the transfer lines were rinsed with a mixture of water (50 mL) and ethanol (50 mL). The filtrate was treated at 20-25° C. within one hour with 25% hydrochloric acid (approx. 280 mL) until the pH was <2.0. The resulting suspension was stirred for one hour at room temperature. The crystals were filtered off, washed with a mixture of ethanol (200 mL) and water (200 mL) and subsequently dried at 50° C./<25 mbar until constant weight to afford 52.0 g (83%) of the title acid as an off-white solid with a purity of 99.5%.

Alternative 2

Telescoped Process

To as suspension of sodium hydride (60% in mineral oil, 3.95 g, 99 mmol, 1.6 eq.) in THF (120 mL) was added within 120 minutes at 25-32° C. a solution of [3-(4-Fluorophenyl)-5-methyl-isoxazol-4-yl]-methanol (12.50 g, 60 mmol) and 6-chloronicotinonitrile (8.36 g, 60 mmol) in THF (60 mL) and the resulting mixture was stirred for one hour at approx. 30° C. The mixture was then treated dropwise at room temperature with water (100 mL). THF was distilled off under reduced pressure (200-70 mbar) with a jacket temperature of 50° C. The residue was diluted with ethanol (90 mL) and subsequently treated at 20 to 35° C. with 28% sodium hydroxide solution (69.6 g, 487 mmol). The mixture was heated to 50-55° C. and subsequently stirred at this temperature for 15 hour. The reaction mixture was treated with toluene (150 mL) and the resulting biphasic mixture was stirred for 15 minutes and the layers were then allowed to separate for 30 minutes. The lower product-containing aqueous layer was separated and the toluene layer was extracted at 30° C. with water (1×50 mL). The combined aqueous layers were acidified with 20% sulfuric acid (approx. 150 g) until a pH of 3.0-3.3 was obtained. The suspension was treated with THF (120 mL) and the resulting biphasic mixture was stirred for 15 minutes and the layers were then allowed to separate for 30 minutes. The lower aqueous layer was removed and the product-containing organic layer was diluted with toluene (150 mL) to afford a biphasic mixture from which the lower aqueous layer was separated. The aqueous layer was removed and the organic layer was washed with water (2×30 mL). From the organic layer THF, Ethanol and water were then completely distilled off under reduced pressure and at a jacket temperature of 40-80° C. and continuously replaced by toluene (250 mL in total). At the end of the distillation a volume of approx. 300 mL was adjusted in the reactor. The partly precipitated product was completely re-dissolved by heating the suspension to 100-105° C. The clear solution was cooled to 15-20° C. within 5-10 hours whereupon crystallization occurred. The crystals were filtered off, washed with toluene (100 mL) and subsequently dried at 55° C./<25 mbar until constant weight to afford 16.81 g (85%) of the title compound as a slightly yellow solid with an assay of 99.2% (w/w).

Alternative 3

Enzymatic Hydrolysis

To 30 ml TRIS/HCl (30 mM) buffer solution at pH 8.1 and 30° C. containing 93.3 mg of the nitrilase (EC 3.5.5.7) from *Acidovorax facilis* [DuPont, distributed by Codexis as nitrilase Nit-107] a solution of 6-[3-(4-Fluoro-phenyl)-5-methyl-isoxazol-4-ylmethoxy]-nicotinonitrile (250 mg, 0.8 mmol) in 1.5 ml DMSO was added forming a suspension under stirring. The pH was kept constant at 8.1 by the addition of 1 N sodium hydroxide. After 2 days the conversion was >95%. Product isolation was started by the addition of filter aid (2 g Dicalite) and n-heptane (30 ml) under vigorous stirring for 30 min. After filtration the lipophilic impurities and remaining substrate were washed out with the heptane phase. The product precipitated during the subsequent pH adjustment of the aqueous phase to pH 1.5 with sulfuric acid. The suspension obtained was extracted once with ethyl acetate (50 ml). After drying with magnesium sulfate the combined ethyl acetate phase was evaporated to afford (176 mg, 66%) of the title compound as a white solid.

Example 11

6-[3-(4-Chloro-phenyl)-isoxazol-4-ylmethoxy]-nicotinic acid

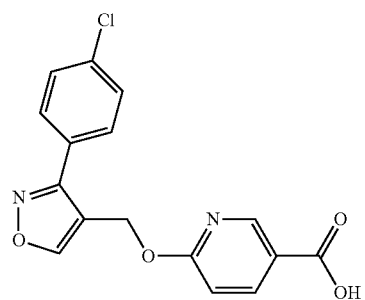 [SMILES: O=C(O)c1ccc(OCc2conc2-c2ccc(Cl)cc2)nc1]

To a suspension of sodium hydride (55% dispersion in mineral oil, 1.16 g, 26.5 mmol) in THF (30 mL) was added a solution of [3-(4-chloro-phenyl)-isoxazol-4-yl]-methanol (24.1 mmol) in THF (60 mL) at 0° C. and the reaction mixture warmed to room temperature over 30 min. Then a solution of methyl 6-chloronicotinate (4.65 g, 26.5 mmol) in THF (60 mL) was added dropwise at 0° C. and the reaction mixture was stirred at room temperature for 2 h. The reaction mixture was then poured into aqueous sodium chloride (saturated) and the mixture was extracted with ethyl acetate. The combined organic layers were then washed with water and brine and then dried over sodium sulfate, filtered and evaporated. Purification by chromatography (SiO$_2$, heptane:ethyl acetate=4:1 to 2:1) afforded 6-[3-(4-Chloro-phenyl)-isoxazol-4-ylmethoxy]-nicotinic acid methyl ester (72%) which was obtained as a light yellow solid. To a suspension of 6-[3-(4-chloro-phenyl)-isoxazol-4-ylmethoxy]-nicotinic acid methyl ester (1.0 mmol) in THF (3 mL) and methanol (3 mL) was added a solution of lithium hydroxide monohydrate (85.1 mg, 2.0 mmol) in water (3 mL) and the resulting mixture stirred at room temperature overnight. The mixture was acidified to pH 4 with HCl (1 N, 30 mL) and the resulting mixture was filtered. The solid was dried to afford the title compound (100%) which was obtained as a light yellow solid. MS: m/e=331.1 [M−H]$^-$.

Example 12

6-[3-(4-Chloro-phenyl)-5-methyl-isoxazol-4-ylmethoxy]-nicotinic acid

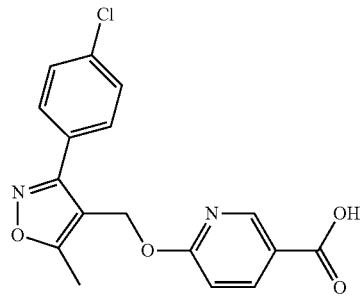 [SMILES: Cc1onc(-c2ccc(Cl)cc2)c1COc1ccc(C(=O)O)cn1]

To a suspension of sodium hydride (55% dispersion in mineral oil, 852 mg, 20 mmol) in THF (27 mL) was added a solution of [3-(3-fluoro-phenyl)-5-methyl-isoxazol-4-yl]-methanol (3.68 g, 18 mmol) in THF (54 mL) at 0° C. and the reaction mixture warmed to room temperature over 30 min. Then a solution of methyl 6-chloronicotinate (3.35 g, 20 mmol) in THF (1.5 mL) was added dropwise at 0° C. and the reaction mixture was stirred at room temperature overnight. The reaction mixture was then poured into aqueous sodium chloride (saturated) and the mixture was extracted with ethyl acetate. The combined organic layers were then washed with water and brine and then dried over sodium sulfate, filtered and evaporated. Purification by chromatography (SiO$_2$, heptane:ethyl acetate=7:3) afforded 6-[3-(4-Chloro-phenyl)-5-methyl-isoxazol-4-ylmethoxy]-nicotinic acid methyl ester (74%) which was obtained as a light yellow solid. To a solution of 6-[3-(4-chloro-phenyl)-5-methyl-isoxazol-4-ylmethoxy]-nicotinic acid methyl ester (1.1 mmol) in THF (5 mL) was added a solution of lithium hydroxide monohydrate (94 mg, 2.2 mmol) in water (5 mL) and methanol (1 mL) added and the resulting mixture stirred at room temperature overnight. The mixture was acidified to pH 4 with HCl (25%, 3 drops) and methanol (2 drops) added. A gum began to form and the mixture was cooled at 0° C. for 1.5 h and then the aqueous layer decanted off. Trituration with diethylether and

Example 13

N-Methyl-6-(5-methyl-3-phenyl-isoxazol-4-yl-methoxy)-N-(tetrahydro-pyran-4-yl)-nicotinamide

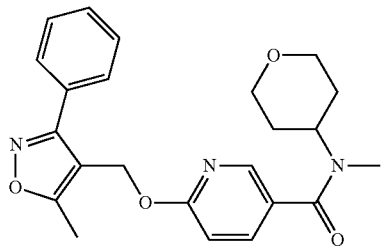 [SMILES: Cc1onc(-c2ccccc2)c1COc1ccc(C(=O)N(C)C2CCOCC2)cn1]

To a solution of 6-(5-methyl-3-phenyl-isoxazol-4-yl-methoxy)-nicotinic acid (200 mg, 0.64 mmol) in DMF (2 mL) were added 2-(1H-benzotriazole-1-yl)-1,1,3,3-tetramethyluronium tetrafluoroborate (228 mg, 0.71 mmol), N,N-diisopropyl ethyl amine (552 µL, 3.22 mmol) and 4-aminotetrahydropyran (0.77 mmol). The resulting reaction mixture was stirred for 12 h at ambient temperature. After dilution with ethyl acetate (20 mL) it was washed with water (20 mL) and aqueous sodium carbonate (saturated, 40 mL). The organic layer was dried over sodium sulfate and concentrated. Purification by chromatography (SiO2, heptane:ethyl acetate=80:20 to 20:80) afforded the title compound (231 mg, 91%) which was obtained as a white solid. MS: m/e=394.1 [M+H]$^+$.

To a solution of 6-(5-methyl-3-phenyl-isoxazol-4-yl-methoxy)-N-(tetrahydro-pyran-4-yl)-nicotinamide (200 mg, 0.51 mmol) in THF (2 mL) was added at 0° C. potassium bis(trimethylsilyl)amide (0.91 M in THF, 614 µL, 0.56 mmol) over a period of 2 min. After stirring for 0.5 h at this temperature iodomethane (41 µL, 0.66 mmol) was added and the resulting suspension was stirred for 2 h at ambient temperature. Concentration and purification by chromatography (SiO2, heptane:ethyl acetate=50:50 to 0:100) afforded the title compound (91 mg, 44%) as a white foam. MS: m/e=408.5 [M+H]$^+$.

Example 14

N-(4-Fluoro-phenyl)-6-(5-methyl-3-phenyl-isoxazol-4-ylmethoxy)-nicotinamide

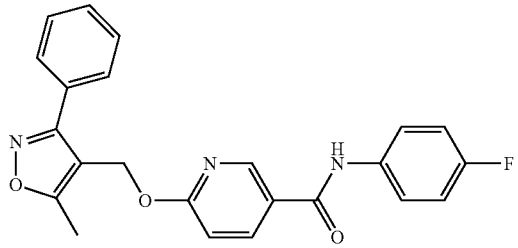 [SMILES: Cc1onc(-c2ccccc2)c1COc1ccc(C(=O)Nc2ccc(F)cc2)cn1]

To a solution of 6-(5-methyl-3-phenyl-isoxazol-4-yl-methoxy)-nicotinic acid (100 mg, 0.32 mmol) in DMF (2 mL) were added 2-(1H-benzotriazole-1-yl)-1,1,3,3-tetramethyluronium tetrafluoroborate (114 mg, 0.35 mmol), N,N-diisopropyl ethyl amine (275 µL, 1.6 mmol) and 4-fluoroaniline (1 M in DMF, 0.35 mmol). The resulting reaction mixture was stirred overnight at room temperature. Concentration and purification by chromatography (SiO2, heptane:ethyl acetate=100:0 to 1:1) afforded the title compound (109 mg, 84%) which was obtained as a white solid. MS: m/e=404.4 [M+H]$^+$.

Example 15

6-(5-Methyl-3-phenyl-isoxazol-4-ylmethoxy)-N-(1-methyl-1H-pyrazol-4-yl)-nicotinamide

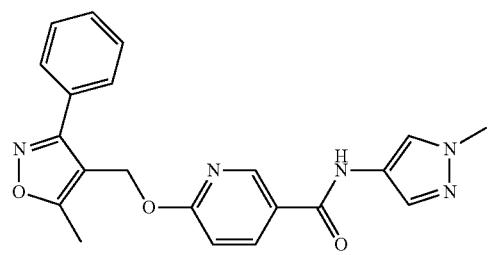 [SMILES: Cc1onc(-c2ccccc2)c1COc1ccc(C(=O)Nc2cnn(C)c2)cn1]

To a solution of 6-(5-methyl-3-phenyl-isoxazol-4-yl-methoxy)-nicotinic acid (100 mg, 0.32 mmol) in DMF (2 mL) were added 2-(1H-benzotriazole-1-yl)-1,1,3,3-tetramethyluronium tetrafluoroborate (114 mg, 0.35 mmol), N,N-diisopropyl ethyl amine (275 µL, 1.6 mmol) and 1-methyl-1H-pyrazol-4-ylamine (1 M solution in MeOH, 0.35 mmol). The resulting reaction mixture was stirred overnight at room temperature. Concentration and purification by chromatography (SiO2, heptane:ethyl acetate=100:0 to 1:1) afforded the title compound (51 mg, 41%) which was obtained as a white solid. MS: m/e=388.1 [M–H]$^-$.

Example 16

N-(3-Isopropyl-isoxazol-5-ylmethyl)-6-(5-methyl-3-phenyl-isoxazol-4-ylmethoxy)-nicotinamide

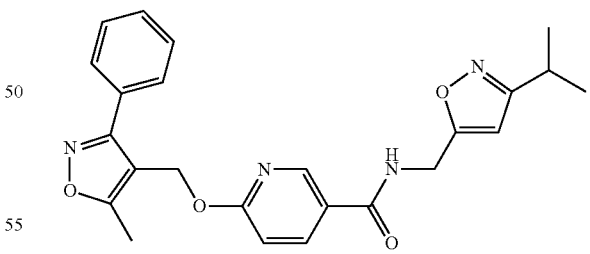

To a solution of 6-(5-methyl-3-phenyl-isoxazol-4-yl-methoxy)-nicotinic acid (100 mg, 0.32 mmol) in DMF (2 mL) were added 2-(1H-benzotriazole-1-yl)-1,1,3,3-tetramethyluronium tetrafluoroborate (114 mg, 0.35 mmol), N,N-diisopropyl ethyl amine (275 µL, 1.6 mmol) and 5-aminomethyl-3-isopropylisoxazole (1 M solution in trifluoroacetic acid, 354 µL, 0.35 mmol). The resulting reaction mixture was stirred overnight at room temperature. Concentration and purification by chromatography (SiO2, heptane:ethyl hexane afforded the title compound (832 mg, 98%) which was obtained as an off white solid. MS: m/e=343.1 [M–H]$^-$.

acetate=100:0 to 1:1) afforded the title compound (112 mg, 81%) which was obtained as a colourless gum. MS: m/e=433.3 [M+H]⁺.

Example 17

6-(5-Methyl-3-phenyl-isoxazol-4-ylmethoxy)-N-pyridin-2-ylmethyl-nicotinamide

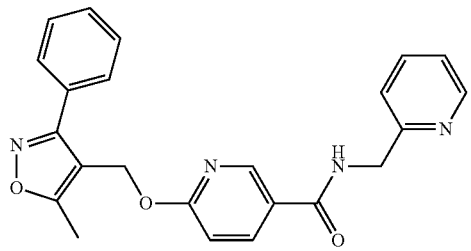 [SMILES: Cc1onc(-c2ccccc2)c1COc1ccc(C(=O)NCc2ccccn2)cn1]

To a solution of 6-(5-methyl-3-phenyl-isoxazol-4-yl-methoxy)-nicotinic acid (200 mg, 0.64 mmol) in DMF (2 mL) were added 2-(1H-benzotriazole-1-yl)-1,1,3,3-tetramethyluronium tetrafluoroborate (228 mg, 0.71 mmol), N,N-diisopropyl ethyl amine (552 µL, 3.22 mmol) and 2-(aminomethyl)pyridine (0.77 mmol). The resulting reaction mixture was stirred for 12 h at ambient temperature. After dilution with ethyl acetate (20 mL) it was washed with water (20 mL) and aqueous sodium carbonate (saturated, 40 mL). The organic layer was dried over sodium sulfate and concentrated. Purification by chromatography ((SiO2, heptane:ethyl acetate:methanol=50:50:0 to 0:95:5) afforded the title compound (191 mg, 74%) which was obtained as a white solid. MS: m/e=401.2 [M+H]⁺.

Example 18

[6-(5-Methyl-3-phenyl-isoxazol-4-ylmethoxy)-pyridin-3-yl]-thiazolidin-3-yl-methanone

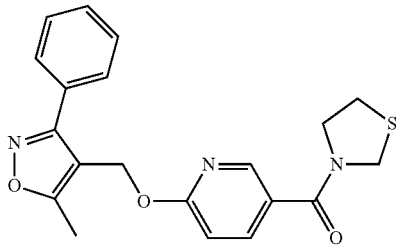 [SMILES: Cc1onc(-c2ccccc2)c1COc1ccc(C(=O)N2CCSC2)cn1]

To a solution of 6-(5-methyl-3-phenyl-isoxazol-4-yl-methoxy)-nicotinic acid (200 mg, 0.65 mmol) and thiazolidine (0.65 mmol) in THF (6 mL) at 0° C. were added 1-hydroxybenzotriazole hydrate (100.8 mg, 0.65 mmol), N-ethyldiisopropylamine (281.7 µl, 1.613 mmol) and N-(3-dimethylaminopropyl)-N'-ethylcarbodiimidazole hydrochloride (126.2 mg, 0.65 mmol). The resulting reaction mixture was stirred overnight at room temperature. Concentration and purification by chromatography (SiO2, heptane:ethyl acetate=3:1 to 1:4) afforded the title compound (68 mg, 28%) which was obtained as a white solid. MS: m/e=382.2 [M+H]⁺.

Example 19

(4-Hydroxy-piperidin-1-yl)-[6-(5-methyl-3-phenyl-isoxazol-4-ylmethoxy)-pyridin-3-yl]-methanone

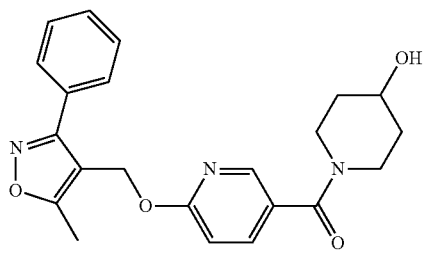 [SMILES: Cc1onc(-c2ccccc2)c1COc1ccc(C(=O)N2CCC(O)CC2)cn1]

To a solution of 6-(5-methyl-3-phenyl-isoxazol-4-yl-methoxy)-nicotinic acid (100 mg, 0.32 mmol) in DMF (2 mL) were added 2-(1H-benzotriazole-1-yl)-1,1,3,3-tetramethyluronium tetrafluoroborate (114 mg, 0.35 mmol), N,N-diisopropyl ethyl amine (275 µL, 1.6 mmol) and 4-hydroxypiperidine (1 M solution in MeOH, 354 µL, 0.35 mmol). The resulting reaction mixture was stirred overnight at room temperature. Concentration and purification by chromatography (SiO2, heptane:ethyl acetate=100:0 to 1:1) afforded the title compound (93 mg, 73%) which was obtained as a white solid. MS: m/e=394.2 [M+H]⁺.

Example 20

(5,6-Dihydro-8H-[1,2,4]triazolo[4,3-a]pyrazin-7-yl)-[6-(5-methyl-3-phenyl-isoxazol-4-ylmethoxy)-pyridin-3-yl]-methanone

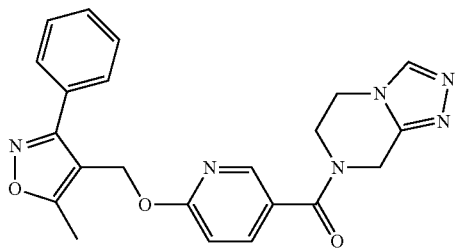 [SMILES: Cc1onc(-c2ccccc2)c1COc1ccc(C(=O)N2CCn3cnnc3C2)cn1]

To a solution of 6-(5-methyl-3-phenyl-isoxazol-4-yl-methoxy)-nicotinic acid (500 mg, 1.6 mmol) in DMF (10 mL) were added 2-(1H-benzotriazole-1-yl)-1,1,3,3-tetramethyluronium tetrafluoroborate (569 mg, 1.8 mmol), N,N-diisopropyl ethyl amine (1.38 mL, 8.1 mmol) and 5,6,7,8-tetrahydro-(1,2,4)triazolo(4,3-a)-pyrazine hydrochloride (1.8 mmol). The resulting reaction mixture was stirred overnight at room temperature. Concentration and purification by chromatography (SiO2, heptane:ethyl acetate=100:0 to 1:1 and then dichloromethane:methanol=9:1) afforded the title compound (605 mg, 86%) which was obtained as a white foam. MS: m/e=417.4 [M+H]+.

Example 21

6-[3-(3-Fluoro-phenyl)-5-methyl-isoxazol-4-yl-methoxy]-N-(2,2,2-trifluoro-ethyl)-nicotinamide

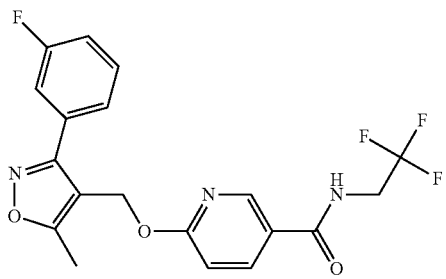 [SMILES: Cc1onc(-c2cccc(F)c2)c1COc1ccc(C(=O)NCC(F)(F)F)cn1]

A solution of trimethylaluminium (2 M in toluene, 600 μL, 1.2 mmol) was added dropwise (exothermic) to a solution of 2,2,2-trifluoroethylamine (119 mg, 94 μL, 1.2 mmol) in dioxane (7.5 mL) and the resulting mixture was stirred at room temperature for 1 h. Then a solution of 6-[3-(3-fluoro-phenyl)-5-methyl-isoxazol-4-ylmethoxy]-nicotinic acid methyl ester (103 mg, 0.3 mmol) in dioxane (4 mL) was added. The resulting mixture was then heated at 85-95° C. for 2 h and then cooled to room temperature and then poured into water and extracted with ethyl acetate which was then washed with brine, dried over sodium sulfate and evaporated. Purification by chromatography (SiO2, heptane:ethyl acetate=100:0 to 1:1) afforded the title compound (122 mg, 99%) which was obtained as a white solid. MS: m/e=410.1 [M+H]+.

Example 22

{6-[3-(3-Fluoro-phenyl)-5-methyl-isoxazol-4-yl-methoxy]-pyridin-3-yl}-thiomorpholin-4-yl-methanone

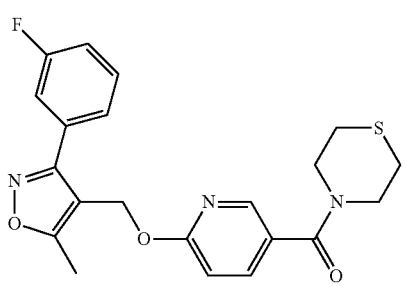 [SMILES: Cc1onc(-c2cccc(F)c2)c1COc1ccc(C(=O)N2CCSCC2)cn1]

A solution of trimethylaluminium (2 M in toluene, 600 μL, 1.2 mmol) was added dropwise (exothermic) to a solution of thiomorpholine (124 mg, 120 μL, 1.2 mmol) in dioxane (7.5 mL) and the resulting mixture was stirred at room temperature for 1 h. Then a solution of 6-[3-(3-fluoro-phenyl)-5-methyl-isoxazol-4-ylmethoxy]-nicotinic acid methyl ester (103 mg, 0.3 mmol) in dioxane (4 mL) was added. The resulting mixture was then heated at 85-95° C. for 4 h and then cooled to room temperature and then poured into water and extracted with ethyl acetate which was then washed with brine, dried over sodium sulfate and evaporated. Purification by chromatography (SiO2, heptane:ethyl acetate=100:0 to 1:3) afforded the title compound (124 mg, 100%) which was obtained as a light yellow gum. MS: m/e=414.4 [M+H]+.

Example 23

N-Cyclopropyl-6-[3-(3-fluoro-phenyl)-5-methyl-isoxazol-4-ylmethoxy]-nicotinamide

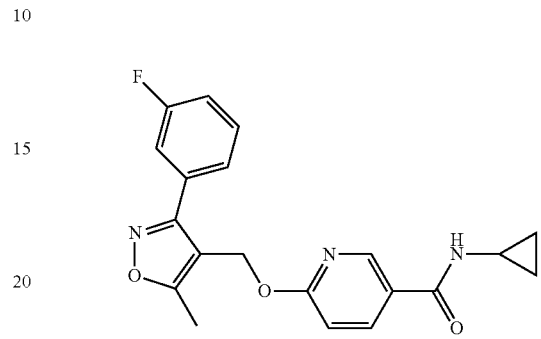

A solution of trimethylaluminium (2 M in toluene, 600 μL, 1.2 mmol) was added dropwise (exothermic) to a solution of cyclopropylamine (69 mg, 84 μL, 1.2 mmol) in dioxane (7.5 mL) and the resulting mixture was stirred at room temperature for 1 h. Then a solution of 6-[3-(3-fluoro-phenyl)-5-methyl-isoxazol-4-ylmethoxy]-nicotinic acid methyl ester (103 mg, 0.3 mmol) in dioxane (4 mL) was added. The resulting mixture was then heated at 85-95° C. for 3 h and then cooled to room temperature and then poured into water and extracted with ethyl acetate which was then washed with brine, dried over sodium sulfate and evaporated. Purification by chromatography (SiO2, heptane:ethyl acetate=100:0 to 1:1) afforded the title compound (100 mg, 91%) which was obtained as a white solid. MS: m/e=368.0 [M+H]+.

Example 24

{6-[3-(3-Chloro-phenyl)-5-methyl-isoxazol-4-yl-methoxy]-pyridin-3-yl}-(1,1-dioxo-1λ6-thiomorpholin-4-yl)-methanone

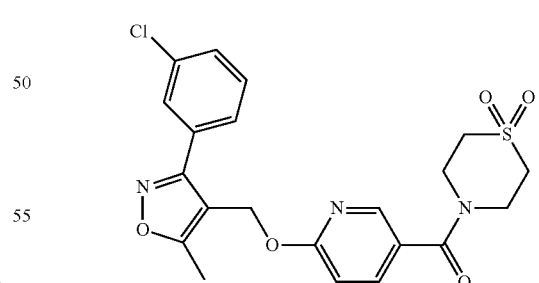

To a solution of 6-[3-(3-chloro-phenyl)-5-methyl-isoxazol-4-ylmethoxy]-nicotinic acid (69 mg, 0.2 mmol) in DMF (300 μL) were added 2-(1H-benzotriazole-1-yl)-1,1,3,3-tetramethyluronium tetrafluoroborate (71 mg, 0.22 mmol), N,N-diisopropyl ethyl amine (171 μL, 1.0 mmol) and thiomorpholine-S,S-dioxide (0.22 mmol). The resulting reaction mixture was stirred for 1 h at room temperature. Concentration and purification by chromatography (SiO2, heptane:

ethyl acetate=100:0 to 1:1) afforded the title compound (80 mg, 87%) which was obtained as a white solid. MS: m/e=462.1 [M+H]+.

Example 25

6-[3-(4-Fluoro-phenyl)-5-methyl-isoxazol-4-yl-methoxy]-N-(tetrahydro-pyran-4-yl)-nicotinamide

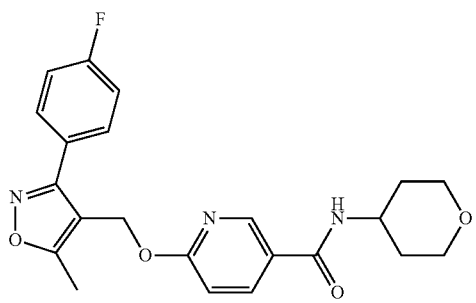 [SMILES: Cc1onc(-c2ccc(F)cc2)c1COc1ccc(C(=O)NC2CCOCC2)cn1]

To a solution of 6-[3-(4-fluoro-phenyl)-5-methyl-isoxazol-4-ylmethoxy]-nicotinic acid (60 mg, 0.2 mmol) in DMF (300 μL) were added 2-(1H-benzotriazole-1-yl)-1,1,3,3-tetramethyluronium tetrafluoroborate (71 mg, 0.22 mmol), N,N-diisopropyl ethyl amine (171 μL, 1.0 mmol) and 4-aminotetrahydropyran (17.3 μL, 0.22 mmol). The resulting reaction mixture was stirred for 1 h at room temperature. Concentration and purification by chromatography (SiO2, heptane:ethyl acetate=100:0 to 1:1) afforded the title compound (38 mg, 85%) which was obtained as a white solid. MS: m/e=412.5 [M+H]+.

Example 26

(1,1-Dioxo-1λ⁶-thiomorpholin-4-yl)-{6-[3-(4-fluoro-phenyl)-5-methyl-isoxazol-4-ylmethoxy]-pyridin-3-yl}-methanone

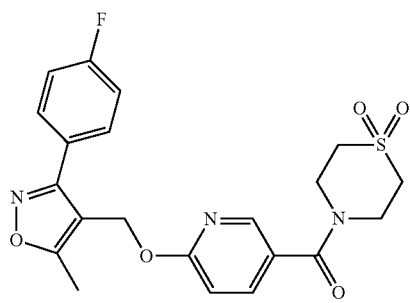 [SMILES: Cc1onc(-c2ccc(F)cc2)c1COc1ccc(C(=O)N2CCS(=O)(=O)CC2)cn1]

Purification of thiomorpholine-1,1-dioxide HCl

A mixture of 60 g of thiomorpholine-1,1-dioxide HCl in 600 mL THF, 105 mL water and 30 mL DMF was heated to 63-66° C. (slightly reflux) and the resulting clear to slightly turbid solution stirred at this temperature for 5 to 10 hours. The mixture was then treated at 63-66° C. within 30 minutes with 300 mL of THF. The mixture was then cooled to 0-5° C. within 3 hours and the resulting suspension stirred at this temperature for an additional hour. The crystals were filtered off, washed with THF (2×25 mL) and dried at 50° C. and under reduced pressure (<20 mbar) to afford 56.6 g (94%) of thiomorpholine-1,1-dioxide HCl with a purity of 100% (area) and a THF content of 0.14%.

(1,1-dioxo-1λ⁶-thiomorpholin-4-yl)-{6-[3-(4-fluoro-phenyl)-5-methyl-isoxazol-4-ylmethoxy]-pyridin-3-yl}-methanone Alternative 1)

6-[3-(4-Fluoro-phenyl)-5-methyl-isoxazol-4-ylmethoxy]-nicotinic acid (23.0 g, 70.1 mmol) and 1,1-carbonyldiimidazole (15.3 g, 94.6 mol, 1.35 eq.) were dissolved in THF (120 mL) and the resulting solution was stirred for one hour at room temperature. This solution was then added to a suspension of thiomorpholine-1,1-dioxide HCl (16.9 g, 98.5 mmol), DMAP (400 mg, 3.27 mmol) and triethylamine (9.78 g, 96.7 mmol) in THF (120 mL). The resulting mixture was heated to reflux temperature and subsequently stirred at this temperature for 50 hours. The mixture was cooled to room temperature and then treated within one hour with water (300 mL). From the resulting suspension THF was distilled off under reduced pressure and with a jacket temperature of 60° C. and continuously replaced by ethanol (426 g) at constant volume. The suspension was cooled to room temperature and stirred for 2 h ours. The crystals were filtered off, washed with a mixture of ethanol (100 mL) and water (100 mL) and subsequently dried at 55° C./<25 mbar until constant weight to afford 28.9 g (92%) of the title compound as a colorless solid with purity of 99.7% (area) as measured by HPLC.

Alternative 2)

To a suspension of thiomorpholine-1,1-dioxide HCl (14.62 g, 0.085 mol) in THF (200 mL) and DMF (50 mL) was added at 38-43° C. within 60 minutes lithium-tert.-butoxide (20% solution in THF; 31.6 g, 0.079 mol) and the resulting solution was stirred at 38-43° C. for 30 minutes. The mixture was then concentrated under reduced pressure at 30-45° C. to volume of 100-120 mL. In a separate second reactor, 6-[3-(4-Fluoro-phenyl)-5-methyl-isoxazol-4-ylmethoxy]-nicotinic acid (20.00 g, 0.061 mmol) was dissolved in THF (55 mL). The solution was then treated at 35-43° C. portionwise within 30 minutes with 1,1-carbonyldiimidazole (11.40 g, 0.070 mol). The resulting mixture was stirred at 37-43° C. for 90-120 minutes and then added at 37-43° C. within 30 to 60 minutes to the thiomorpholine-1,1-dioxide solution prepared above. The first vessel and the transfer lines were rinsed with THF (20 mL). The resulting mixture was stirred for at least 3 hours. Water (60 mL) was then added at 37-43° C. within 30 minutes and the resulting solution was heated to 50-55° C. and stirred for 15-30 minutes. Water (160 mL) was then added at this temperature within 60 minutes. After the addition of approx. 60 mL of water the product started to crystallize. The resulting suspension was subsequently cooled to 15-20° C. within 2-4 h. The crystals were filtered off, washed with water (160 mL) and dried at 55° C./<25 mbar until constant weight to afford 26.89 g (97%) of the title compound as a colorless solid with an assay of 97.2% (w/w) and a purity of 100% (area) as measured by HPLC. The product can be purified to assays

Example 27

6-[3-(4-Fluoro-phenyl)-5-methyl-isoxazol-4-yl-methoxy]-N-isopropyl-nicotinamide

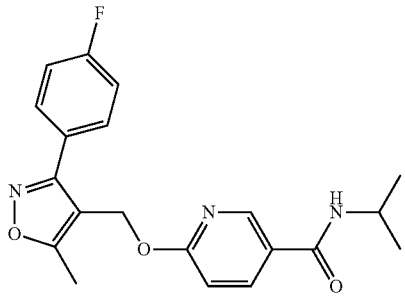 [SMILES: Cc1onc(-c2ccc(F)cc2)c1COc1ccc(C(=O)NC(C)C)cn1]

To a solution of 6-[3-(4-fluoro-phenyl)-5-methyl-isoxazol-4-ylmethoxy]-nicotinic acid (60 mg, 0.2 mmol) in DMF (300 μL) were added 2-(1H-benzotriazole-1-yl)-1,1,3,3-tetramethyluronium tetrafluoroborate (71 mg, 0.22 mmol), N,N-diisopropyl ethyl amine (171 μL, 1.0 mmol) and isopropylamine (0.22 mmol). The resulting reaction mixture was stirred for 1 h at room temperature. Concentration and purification by chromatography (SiO$_2$, heptane:ethyl acetate=100:0 to 1:1) afforded the title compound (53 mg, 79%) which was obtained as an off white solid. MS: m/e=370.0 [M+H]$^+$.

Example 28

N-Cyclopropylmethyl-6-[3-(4-fluoro-phenyl)-5-methyl-isoxazol-4-ylmethoxy]-nicotinamide

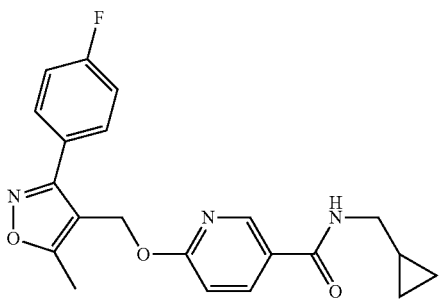 [SMILES: Cc1onc(-c2ccc(F)cc2)c1COc1ccc(C(=O)NCC2CC2)cn1]

To a solution of 6-[3-(4-fluoro-phenyl)-5-methyl-isoxazol-4-ylmethoxy]-nicotinic acid (60 mg, 0.2 mmol) in DMF (300 μL) were added 2-(1H-benzotriazole-1-yl)-1,1,3,3-tetramethyluronium tetrafluoroborate (71 mg, 0.22 mmol), N,N-diisopropyl ethyl amine (171 μL, 1.0 mmol) and cyclopropanemethylamine (0.22 mmol). The resulting reaction mixture was stirred for 1 h at room temperature. Concentration and purification by chromatography (SiO$_2$, heptane:ethyl acetate=100:0 to 1:1) afforded the title compound (45 mg, 65%) which was obtained as a white solid. MS: m/e=382.4 [M+H]$^+$.

Example 29

{6-[3-(4-Fluoro-phenyl)-5-methyl-isoxazol-4-yl-methoxy]-pyridin-3-yl}-morpholin-4-yl-methanone

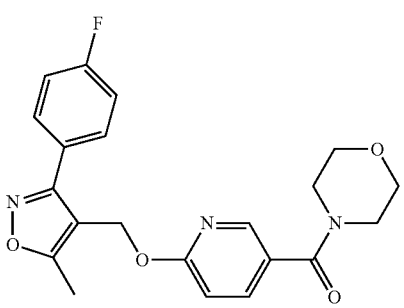 [SMILES: Cc1onc(-c2ccc(F)cc2)c1COc1ccc(C(=O)N2CCOCC2)cn1]

To a solution of 6-[3-(4-fluoro-phenyl)-5-methyl-isoxazol-4-ylmethoxy]-nicotinic acid (60 mg, 0.2 mmol) in DMF (300 μL) were added 2-(1H-benzotriazole-1-yl)-1,1,3,3-tetramethyluronium tetrafluoroborate (71 mg, 0.22 mmol), N,N-diisopropyl ethyl amine (171 μL, 1.0 mmol) and morpholine (0.22 mmol). The resulting reaction mixture was stirred for 1 h at room temperature. Concentration and purification by chromatography (SiO$_2$, heptane:ethyl acetate=100:0 to 1:1) afforded the title compound (10 mg, 13%) which was obtained as a white solid. MS: m/e=398.3 [M+H]$^+$.

Example 30

6-[3-(4-Fluoro-phenyl)-5-methyl-isoxazol-4-yl-methoxy]-N-(2,2,2-trifluoro-ethyl)-nicotinamide

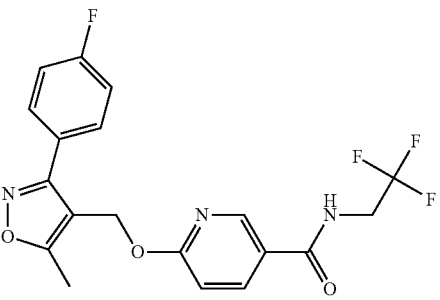 [SMILES: Cc1onc(-c2ccc(F)cc2)c1COc1ccc(C(=O)NCC(F)(F)F)cn1]

To a solution of 6-[3-(4-fluoro-phenyl)-5-methyl-isoxazol-4-ylmethoxy]-nicotinic acid (60 mg, 0.2 mmol) in DMF (300 μL) were added 2-(1H-benzotriazole-1-yl)-1,1,3,3-tetramethyluronium tetrafluoroborate (71 mg, 0.22 mmol), N,N-diisopropyl ethyl amine (171 μL, 1.0 mmol) and 2,2,2-trifluoroethylamine (17.3 μL, 0.22 mmol). The resulting reaction mixture was stirred for 1 h at room temperature. Concentration and purification by chromatography (SiO$_2$, heptane:

ethyl acetate=100:0 to 1:1) afforded the title compound (37 mg, 50%) which was obtained as a white solid. MS: m/e=410.4 [M+H]⁺.

Example 31

6-[3-(4-Chloro-phenyl)-isoxazol-4-ylmethoxy]-N-isopropyl-nicotinamide

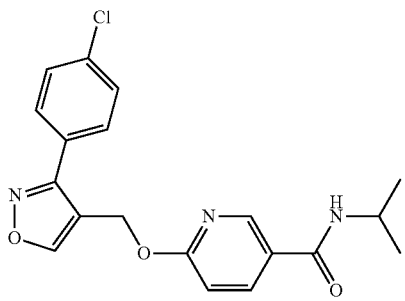 [SMILES: CC(C)NC(=O)c1ccc(OCc2conc2-c2ccc(Cl)cc2)nc1]

A solution of trimethylaluminium (2 M in toluene, 1.17 mL, 2.3 mmol) was added dropwise (exothermic) to a solution of isopropylamine (2.3 mmol) in dioxane (15 mL) and the resulting mixture was stirred at room temperature for 1.5 h. Then 6-[3-(4-chloro-phenyl)-isoxazol-4-ylmethoxy]-nicotinic acid methyl ester (200 mg, 0.58 mmol) was added. The resulting mixture was then heated at 85° C. for 2 h and then cooled to room temperature and then poured into water and extracted with ethyl acetate which was then washed with brine, dried over sodium sulfate and evaporated. Purification by chromatography (SiO2, heptane:ethyl acetate=2:1 to 1:1) afforded the title compound (120 mg, 56%) which was obtained as a white solid. MS: m/e=372.1 [M+H]⁺.

Example 32

6-[3-(4-Chloro-phenyl)-isoxazol-4-ylmethoxy]-N-(3-hydroxy-propyl)-nicotinamide

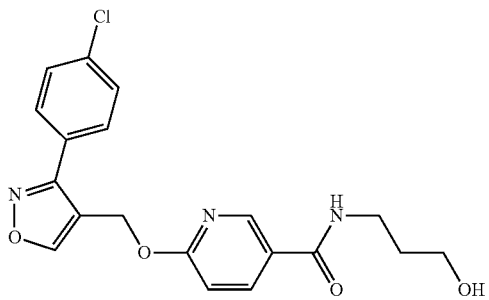 [SMILES: O=C(NCCCO)c1ccc(OCc2conc2-c2ccc(Cl)cc2)nc1]

To a solution of 6-[3-(4-chloro-phenyl)-isoxazol-4-ylmethoxy]-nicotinic acid (200 mg, 0.6 mmol) and 3-amino-1-propanol (0.65 mmol) in THF (6 mL) at 0° C. were added 1-hydroxybenzotriazole hydrate (100.8 mg, 0.65 mmol), N-ethyldiisopropylamine (281.7 µl, 1.613 mmol) and N-(3-dimethylaminopropyl)-N'-ethylcarbodiimidazole hydrochloride (126.2 mg, 0.65 mmol). The resulting reaction mixture was stirred overnight at room temperature. Concentration and purification by chromatography (SiO2, heptane:ethyl acetate=3:1 to 1:4) afforded the title compound (73 mg, 70%) which was obtained as a white solid. MS: m/e=374.0 [M+H]⁺.

Example 33

6-[3-(4-Chloro-phenyl)-5-methyl-isoxazol-4-yl-methoxy]-N-cyclopropylmethyl-nicotinamide

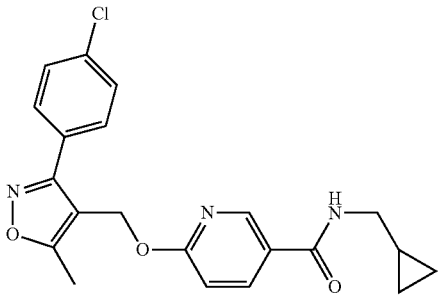 [SMILES: Cc1onc(-c2ccc(Cl)cc2)c1COc1ccc(C(=O)NCC2CC2)cn1]

A solution of trimethylaluminium (2 M in toluene, 401 µL, 0.8 mmol) was added dropwise (exothermic) to a solution of cyclopropanemethylamine (0.8 mmol) in dioxane (5 mL) and the resulting mixture was stirred at room temperature for 1 h. Then a solution of 6-[3-(4-chloro-phenyl)-5-methyl-isoxazol-4-ylmethoxy]-nicotinic acid methyl ester (72 mg, 0.2 mmol) in dioxane (2.5 mL) was added. The resulting mixture was then heated at 85-95° C. for 1 h and then cooled to room temperature and then poured into water and extracted with ethyl acetate which was then washed with brine, dried over sodium sulfate and evaporated. Purification by chromatography (SiO2, heptane:ethyl acetate=100:0 to 1:1) afforded the title compound (56 mg, 70%) which was obtained as a white solid. MS: m/e=398.4 [M+H]⁺.

Example 34

6-[3-(4-Chloro-phenyl)-5-methyl-isoxazol-4-yl-methoxy]-N-(1-methyl-1H-pyrazol-4-yl)-nicotinamide

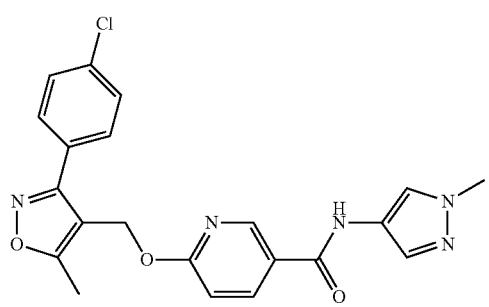 [SMILES: Cc1onc(-c2ccc(Cl)cc2)c1COc1ccc(C(=O)Nc2cnn(C)c2)cn1]

To a solution of 6-[3-(4-chloro-phenyl)-5-methyl-isoxazol-4-ylmethoxy]-nicotinic acid (224 mg, 0.65 mmol) and 1-methyl-1H-pyrazol-4-ylamine (0.65 mmol) in THF (6 mL) at 0° C. were added 1-hydroxybenzotriazole hydrate (100.8 mg, 0.65 mmol), N-ethyldiisopropylamine (281.7 µl, 1.613 mmol) and N-(3-dimethylaminopropyl)-N'-ethylcarbodiimidazole hydrochloride (126.2 mg, 0.65 mmol). The resulting reaction mixture was stirred overnight at room temperature.

Concentration and purification by chromatography (SiO2, heptane:ethyl acetate=3:1 to 1:4) afforded the title compound (201 mg, 73%) which was obtained as a white solid. MS: m/e=424.2 [M+H]⁺.

The invention claimed is:

1. A process for the preparation of a compound of formula (I) or pharmaceutically acceptable salts thereof

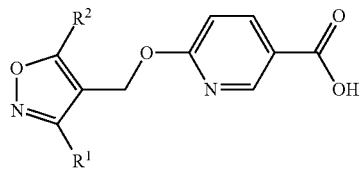

wherein R¹ is phenyl optionally substituted by one or more halogen and R² is hydrogen, alkyl or haloalkyl; which comprises:
a) the hydrolysis of a compound of formula (IV) in a solvent, in the presence of 7 to 10 eq. of base, at a temperature between 50° C. and 60° C.,

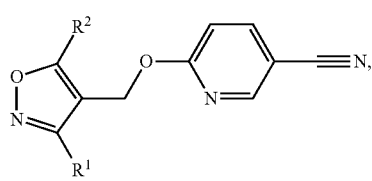

b) removal of impurities by filtration; followed by
c) addition of an acid, in a solvent; followed by
d) filtration, washing with an alcohol/water mixture and drying of the thereby obtained crystals of a compound of formula (I).

2. The process according to claim 1, wherein R¹ is phenyl, or phenyl substituted by one fluoro, or phenyl substituted by one chloro.

3. The process of claim 2, wherein R¹ is 4-fluoro-phenyl.

4. The process of claim 1, wherein R² is hydrogen or methyl.

5. The process of claim 4, wherein R² is methyl.

6. The process of claim 1, wherein the solvent employed in step a) is a mixture of water with methanol, water with ethanol or water with isopropanol.

7. The process of claim 1, wherein the base employed in step a) is sodium hydroxide, potassium hydroxide or lithium hydroxide.

8. The process of claim 1, wherein the acid employed in step c) is aqueous hydrochloric acid or aqueous sulfuric acid and wherein the solvent employed in step c) is water.

9. The process of claim 1, wherein the compound of formula (IV) is prepared by reaction of a compound of formula (II)

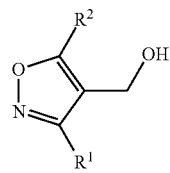

with a compound of formula (III)

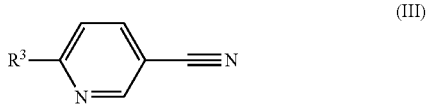

wherein R³ is a leaving group selected from halogen, —OS(O)₂-alkyl, or —OS(O)₂-aryl, in the presence of a base, said process comprising:
a) dissolution of a compound of formula (II) together with a compound of formula (III) in a solvent; followed by
b) addition of this solution to a suspension of a base in a solvent and reaction; followed by
c) neutralization by addition of an acid in a solvent; followed by
d) isolation of the compound of formula (IV) by a solvent exchange to alcohol/water and subsequent filtration and drying.

10. The process of claim 9, wherein R³ is chloro, bromo, iodo, methanesulfonate, or toluene-4-sulfonate.

11. The process of claim 10, wherein R³ is chloro.

12. The process of claim 9, wherein the solvent employed in step a) is THF or MeTHF.

13. The process of claim 9, wherein the base employed in step b) is sodium hydride or sodium tert-butoxide, and wherein the solvent employed in step b) is THF or MeTHF.

14. The process of claim 9, wherein the acid employed in step c) is citric acid, and wherein the solvent employed in step c) is water.

15. The process of claim 9, wherein in step d) the solvent is exchanged to a mixture of water with methanol, water with ethanol or water with isopropanol.

16. A process, for the preparation of a compound of formula (I) or pharmaceutically acceptable salts thereof

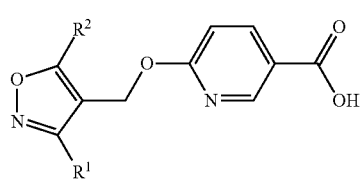

wherein R¹ is phenyl optionally substituted by one or more halogen and R² is hydrogen, alkyl or haloalkyl; which comprises the reaction of a compound of formula (IV)

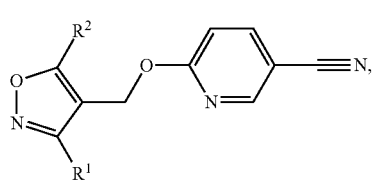

to a compound of formula (I) or pharmaceutically acceptable salts thereof wherein further the compound of formula (IV) is prepared by reaction of a compound of formula (II)

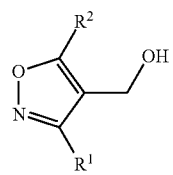

with a compound of formula (III)

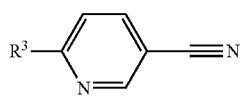

wherein $R^3$ is a leaving group selected from halogen, —OS(O)$_2$-alkyl, or —OS(O)$_2$-aryl, in the presence of a base wherein the compound of formula (I) is prepared in a telescoped process through reaction of a compound of formula (II) with a compound of formula (III) to a compound of formula (IV), followed by directly converting the compound of formula (IV) without isolating it to a compound of formula (I), wherein:
a) dissolution of a compound of formula (II) together with a compound of formula (III) in a solvent; followed by
b) addition of this solution to a suspension of a base in a solvent and reaction; followed by
c) quenching of the reaction; followed by
d) solvent exchange to alcohol/water; followed by
e) treatment with a base, in a solvent; followed by
f) washing the aqueous reaction mixture with a solvent to remove impurities; followed by
g) acidification of the aqueous phase with an acid; followed by
h) extraction of the compound of formula (I) with a solvent; followed by
i) crystallization from a solvent to yield compounds of formula (I).

17. The telescoped process of claim 16, wherein the suspension of a base employed in step b) is a suspension of sodium hydride in THF or MeTHF.

18. The telescoped process of claim 16, wherein the reaction is quenched with water in step c).

19. The telescoped process of claim 16, wherein the solvent exchange in step d) is performed to a mixture of water with methanol, water with ethanol or water with isopropanol.

20. The telescoped process of claim 16, wherein the base employed in step e) is sodium hydroxide, potassium hydroxide or lithium hydroxide and wherein the solvent employed in step e) is a mixture of water with methanol, water with ethanol or water with isopropanol.

21. The telescoped process of claim 16, wherein the solvent employed in step f) is toluene.

22. The telescoped process of claim 16, wherein the acid employed in step g) is aqueous hydrochloric acid or aqueous sulfuric acid.

23. The telescoped process of claim 16, wherein the solvent employed in step h) is THF, toluene or a mixture of THF/toluene.

24. The telescoped process of claim 16, wherein the solvent employed in step i) is toluene.

25. The process of claim 16, wherein the compound of formula (IV) is converted to a compound of formula (I) using a biocatalytic process.

26. The biocatalytic process of claim 16, wherein a biocatalyst is reacted with compounds of formula (IV) in an aqueous buffer.

27. The biocatalytic process of claim 16, wherein pH of the reaction mixture is kept constant at the selected value by the addition of a base.

28. The biocatalytic process of claim 16, wherein the pH is kept constant with a base selected from aqueous NaOH or aqueous KOH.

29. The biocatalytic process of claim 16, wherein the biocatalyst employed is a whole microbial cell.

30. The biocatalytic process of claim 16, wherein the biocatalyst employed is microbial strain *Fusarium poae* [ATCC 24668].

31. The biocatalytic process of claim 16, wherein the biocatalyst employed is an enzyme.

32. The biocatalytic process of claim 31, wherein the biocatalyst employed is a nitrilase selected from Nit-103, Nit-104, Nit-107, Nit-108, Nit-121, Nit-122, Nit-124 and Nit-127$_1$.

33. The biocatalytic process of claim 26, wherein the aqueous buffer used is selected from the group of N,N-bis(2-hydroxyethyl)glycine (Bicine), 4-2-hydroxyethyl-1-piperazineethanesulfonic acid (HEPES), 2-(N-morpholino)ethanesulfonic acid (MES), 3-(N-morpholino)propanesulfonic acid (MOPS), phosphate buffer saline (PBS), piperazine-N,N'-bis(2-ethanesulfonic acid) (PIPES), saline sodium citrate (SSC), 3-{[tris(hydroxymethyl)-methyl]-amino}-propanesulfonic acid (TAPS), 2-{[tris(hydroxymethyl)-methyl]-amino}ethanesulfonic acid (TES), N-tris(hydroxymethyl)-methylglycine (Tricine), and tris(hydroxymethyl)-methylamine (TRIS), or mixtures thereof.

34. The process of claim 1, wherein the compound of formula (IV) is selected from the group consisting of:
6-[3-(3-Fluoro-phenyl)-5-methyl-isoxazol-4-ylmethoxy]-nicotinonitrile;
6-[3-(3-Chloro-phenyl)-5-methyl-isoxazol-4-ylmethoxy]-nicotinonitrile;
6-[3-(4-Fluoro-phenyl)-5-methyl-isoxazol-4-ylmethoxy]-nicotinonitrile;
6-[3-(4-Chloro-phenyl)-isoxazol-4-ylmethoxy]-nicotinonitrile; and
6-[3-(4-Chloro-phenyl)-5-methyl-isoxazol-4-ylmethoxy]-nicotinonitrile.

35. The process of claim 34, wherein the compound of formula (IV) is 6-[3-(4-Fluoro-phenyl)-5-methyl-isoxazol-4-ylmethoxy]-nicotinonitrile.

36. The process of claim 1, wherein the compound of formula (I) is selected from the group consisting of:
6-(5-Methyl-3-phenyl-isoxazol-4-ylmethoxy)-nicotinic acid;
6-[3-(3-Fluoro-phenyl)-5-methyl-isoxazol-4-ylmethoxy]-nicotinic acid;
6-[3-(3-Chloro-phenyl)-5-methyl-isoxazol-4-ylmethoxy]-nicotinic acid;
6-[3-(4-Fluoro-phenyl)-5-methyl-isoxazol-4-ylmethoxy]-nicotinic acid;
6-[3-(4-Chloro-phenyl)-isoxazol-4-ylmethoxy]-nicotinic acid; and
6-[3-(4-Chloro-phenyl)-5-methyl-isoxazol-4-ylmethoxy]-nicotinic acid; and salts thereof.

37. The process of claim 36, wherein the compound of formula (I) is 6-[3-(4-Fluoro-phenyl)-5-methyl-isoxazol-4-ylmethoxy]-nicotinic acid; or salts thereof.

38. The process of claim 1, further comprising the reaction of a compound of formula (I) or salts thereof with a compound of formula (V) or salts thereof,

wherein R⁸ and R⁹ are independently selected from the group of hydrogen, alkyl, haloalkyl, hydroxyalkyl, cycloalkyl, cycloalkylalkyl, heterocycloalkyl, heterocycloalkylalkyl, aryl, arylalkyl, heteroaryl, and heteroarylalkyl, wherein cycloalkyl, heterocycloalkyl, aryl and heteroaryl are optionally substituted with one or more halogen, CN, alkyl, alkoxy, haloalkyl, hydroxyalkyl, hydroxy, or oxo;
or R⁸ and R⁹ together with the nitrogen to which they are attached to form a heterocycloalkyl or heteroaryl, wherein heterocycloalkyl and heteroaryl are optionally substituted with one or more halogen, CN, alkyl, alkoxy, haloalkyl, hydroxyalkyl, hydroxy, or oxo;
with the proviso that R⁸ and R⁹ are not both hydrogen;
to a compound of formula (VI) or pharmaceutically acceptable salts thereof

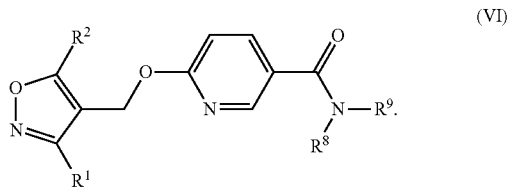

39. The process according to claim 38, wherein the reaction is selected from the group consisting of:
i) the reaction of a compound of formula (I) or salts thereof, in a solvent, such as DMF, in the presence of TBTU and DIPEA, together with a compound of formula (V), in a solvent, such as methanol, to give a compound of formula (VI); or
ii) the reaction of a compound of formula (I) or salts thereof, in a solvent, such as THF, in the presence of HOBT, DIPEA and EDAC, together with a compound of formula (V), to give a compound of formula (VI); or
iii) the reaction of a compound of formula (I) or salts thereof, in a solvent, such as DMF or THF, in the presence of CDI, together with a compound of formula (V), in a solvent, to give a compound of formula (VI); or
iv) the reaction of a compound of formula (I) or salts or esters thereof, in a solvent, such as toluene, in the presence of Me₃Al, together with a compound of formula (V), in a solvent, such as dioxane, to give a compound of formula (VI); or
v) the reaction of a compound of formula (I) or salts or esters thereof, in a solvent, such as toluene, in the presence of TBD, together with a compound of formula (V), to give a compound of formula (VI); or
vi) the reaction of a compound of formula (I) or salts thereof, in a solvent, such as THF, in the presence of CDI, with or without DMAP, and a base such as triethylamine (TEA), together with a compound of formula (V), to give a compound of formula (VI).

40. The process of claim 38, wherein the compound of formula (V) is employed in a salt form, in particularly as a hydrochloric salt, which is converted to the free base of the compound of formula (V) by reaction with lithium tert-butoxide (LiOtBu), in a solvent prior to reaction with a compound of formula (I).

41. The process of claim 38, wherein R⁸ is isopropyl, trifluoroethyl, hydroxypropyl, cyclopropyl, cyclopropylmethyl, tetrahydropyranyl, isoxazolylmethyl substituted by isopropyl, phenyl substituted by fluoro, pyrazolyl substituted by methyl, or pyridinylmethyl.

42. The process of claim 38, wherein R⁹ is hydrogen or methyl.

43. The process of claim 38, wherein R⁸ and R⁹ together with the nitrogen to which they are attached to form thiazolidinyl, piperidinyl substituted by hydroxy, morpholinyl, thiomorpholinyl, 1,1-dioxo-thiomorpholin-4-yl, or 5,6-Dihydro-8H-[1,2,4]triazolo[4,3-a]pyrazin-7-yl.

44. The process of claim 43, wherein R⁸ and R⁹ together with the nitrogen to which they are attached to form morpholinyl, or 1,1-dioxo-thiomorpholin-4-yl.

45. The process of claim 44, wherein the compound of formula (V) is thiomorpholine-1,1-dioxide or thiomorpholine-1,1-dioxide HCl.

46. The process of claim 38, wherein the compound of formula (VI) is selected from the group consisting of:
N-Methyl-6-(5-methyl-3-phenyl-isoxazol-4-ylmethoxy)-N-(tetrahydro-pyran-4-yl)-nicotinamide;
N-(4-Fluoro-phenyl)-6-(5-methyl-3-phenyl-isoxazol-4-ylmethoxy)-nicotinamide;
6-(5-Methyl-3-phenyl-isoxazol-4-ylmethoxy)-N-(1-methyl-1H-pyrazol-4-yl)-nicotinamide;
N-(3-Isopropyl-isoxazol-5-ylmethyl)-6-(5-methyl-3-phenyl-isoxazol-4-ylmethoxy)-nicotinamide;
6-(5-Methyl-3-phenyl-isoxazol-4-ylmethoxy)-N-pyridin-2-ylmethyl-nicotinamide;
[6-(5-Methyl-3-phenyl-isoxazol-4-ylmethoxy)-pyridin-3-yl]-thiazolidin-3-yl-methanone;
(4-Hydroxy-piperidin-1-yl)-[6-(5-methyl-3-phenyl-isoxazol-4-ylmethoxy)-pyridin-3-yl]-methanone;
(5,6-Dihydro-8H-[1,2,4]triazolo[4,3-a]pyrazin-7-yl)-[6-(5-methyl-3-phenyl-isoxazol-4-ylmethoxy)-pyridin-3-yl]-methanone;
6-[3-(3-Fluoro-phenyl)-5-methyl-isoxazol-4-ylmethoxy]-N-(2,2,2-trifluoro-ethyl)-nicotinamide;
{6-[3-(3-Fluoro-phenyl)-5-methyl-isoxazol-4-ylmethoxy]-pyridin-3-yl}-thiomorpholin-4-yl-methanone;
N-Cyclopropyl-6-[3-(3-fluoro-phenyl)-5-methyl-isoxazol-4-ylmethoxy]-nicotinamide;
{6-[3-(3-Chloro-phenyl)-5-methyl-isoxazol-4-ylmethoxy]-pyridin-3-yl}-(1,1-dioxo-1λ⁶-thiomorpholin-4-yl)-methanone;
6-[3-(4-Fluoro-phenyl)-5-methyl-isoxazol-4-ylmethoxy]-N-(tetrahydro-pyran-4-yl)-nicotinamide;
(1,1-dioxo-1λ⁶-thiomorpholin-4-yl)-{6-[3-(4-fluoro-phenyl)-5-methyl-isoxazol-4-ylmethoxy]-pyridin-3-yl}-methanone;
6-[3-(4-Fluoro-phenyl)-5-methyl-isoxazol-4-ylmethoxy]-N-isopropyl-nicotinamide;
N-Cyclopropylmethyl-6-[3-(4-fluoro-phenyl)-5-methyl-isoxazol-4-ylmethoxy]-nicotinamide;
{6-[3-(4-Fluoro-phenyl)-5-methyl-isoxazol-4-ylmethoxy]-pyridin-3-yl}-morpholin-4-yl-methanone;
6-[3-(4-Fluoro-phenyl)-5-methyl-isoxazol-4-ylmethoxy]-N-(2,2,2-trifluoro-ethyl)-nicotinamide;
6-[3-(4-Chloro-phenyl)-isoxazol-4-ylmethoxy]-N-isopropyl-nicotinamide;
6-[3-(4-Chloro-phenyl)-isoxazol-4-ylmethoxy]-N-(3-hydroxy-propyl)-nicotinamide;
6-[3-(4-Chloro-phenyl)-5-methyl-isoxazol-4-ylmethoxy]-N-cyclopropylmethyl-nicotinamide;
and 6-[3-(4-Chloro-phenyl)-5-methyl-isoxazol-4-ylmethoxy]-N-(1-methyl-1H-pyrazol-4-yl)-nicotinamide; and pharmaceutically acceptable salts thereof.

47. The process of claim 46, wherein the compound of formula (VI) is selected from the group consisting of:
  6-[3-(4-Fluoro-phenyl)-5-methyl-isoxazol-4-ylmethoxy]-N-(tetrahydro-pyran-4-yl)-nicotinamide;
  (1,1-dioxo-1λ⁶-thiomorpholin-4-yl)-{6-[3-(4-fluoro-phenyl)-5-methyl-isoxazol-4-ylmethoxy]-pyridin-3-yl}-methanone;
  6-[3-(4-Fluoro-phenyl)-5-methyl-isoxazol-4-ylmethoxy]-N-isopropyl-nicotinamide;
  N-Cyclopropylmethyl-6-[3-(4-fluoro-phenyl)-5-methyl-isoxazol-4-ylmethoxy]-nicotinamide;
  {6-[3-(4-Fluoro-phenyl)-5-methyl-isoxazol-4-ylmethoxy]-pyridin-3-yl}-morpholin-4-yl-methanone; and
  6-[3-(4-Fluoro-phenyl)-5-methyl-isoxazol-4-ylmethoxy]-N-(2,2,2-trifluoro-ethyl)-nicotinamide;
  and pharmaceutically acceptable salts thereof.

48. The process of claim 47, wherein the compound of formula (VI) is (1,1-dioxo-1λ⁶-thiomorpholin-4-yl)-{6-[3-(4-fluoro-phenyl)-5-methyl-isoxazol-4-ylmethoxy]-pyridin-3-yl}-methanone; or pharmaceutically acceptable salts thereof.

49. A process for the preparation of a compound of formula (VI) according to claim 38, comprising the reaction of a compound of formula (II) with a compound of formula (III) to a compound of formula (IV),
  followed by the reaction of the compound of formula (IV) to a compound of formula (I),
  followed by the reaction of the compound of formula (I) with a compound of formula (V) to a compound of formula (VI);
  wherein the compound of formula (II) is 3-(4-Fluoro-phenyl)-5-methyl-isoxazol-4-ylmethanol,
  wherein the compound of formula (III) is 6-chloronicotinonitrile,
  wherein the compound of formula (IV) is 6-[3-(4-Fluoro-phenyl)-5-methyl-isoxazol-4-ylmethoxy]-nicotinonitrile,
  wherein the compound of formula (I) is 6-[3-(4-Fluoro-phenyl)-5-methyl-isoxazol-4-ylmethoxy]-nicotinic acid, or salts thereof;
  wherein the compound of formula (V) is thiomorpholine-1,1-dioxide, or salts thereof;
  wherein the compound of formula (VI) is (1,1-dioxo-1λ⁶-thiomorpholin-4-yl)-{6-[3-(4-fluoro-phenyl)-5-methyl-isoxazol-4-ylmethoxy]-pyridin-3-yl}-methanone, or pharmaceutically acceptable salts thereof.

50. The process of claim 16, wherein the compound of formula (IV) is selected from the group consisting of:
  6-[3-(3-Fluoro-phenyl)-5-methyl-isoxazol-4-ylmethoxy]-nicotinonitrile;
  6-[3-(3-Chloro-phenyl)-5-methyl-isoxazol-4-ylmethoxy]-nicotinonitrile;
  6-[3-(4-Fluoro-phenyl)-5-methyl-isoxazol-4-ylmethoxy]-nicotinonitrile;
  6-[3-(4-Chloro-phenyl)-isoxazol-4-ylmethoxy]-nicotinonitrile; and
  6-[3-(4-Chloro-phenyl)-5-methyl-isoxazol-4-ylmethoxy]-nicotinonitrile.

51. The process of claim 50, wherein the compound of formula (IV) is 6-[3-(4-Fluoro-phenyl)-5-methyl-isoxazol-4-ylmethoxy]-nicotinonitrile.

52. The process of claim 51, wherein the compound of formula (I) is selected from the group consisting of:
  6-(5-Methyl-3-phenyl-isoxazol-4-ylmethoxy)-nicotinic acid;
  6-[3-(3-Fluoro-phenyl)-5-methyl-isoxazol-4-ylmethoxy]-nicotinic acid;
  6-[3-(3-Chloro-phenyl)-5-methyl-isoxazol-4-ylmethoxy]-nicotinic acid;
  6-[3-(4-Fluoro-phenyl)-5-methyl-isoxazol-4-ylmethoxy]-nicotinic acid;
  6-[3-(4-Chloro-phenyl)-isoxazol-4-ylmethoxy]-nicotinic acid; and
  6-[3-(4-Chloro-phenyl)-5-methyl-isoxazol-4-ylmethoxy]-nicotinic acid; and salts thereof.

53. The process of claim 52, wherein the compound of formula (I) is 6-[3-(4-Fluoro-phenyl)-5-methyl-isoxazol-4-ylmethoxy]-nicotinic acid; or salts thereof.

54. The process of claim 16, further comprising the reaction of a compound of formula (I) or salts thereof with a compound of formula (V) or salts thereof,

wherein R⁸ and R⁹ are independently selected from the group of hydrogen, alkyl, haloalkyl, hydroxyalkyl, cycloalkyl, cycloalkylalkyl, heterocycloalkyl, heterocycloalkylalkyl, aryl, arylalkyl, heteroaryl, and heteroarylalkyl, wherein cycloalkyl, heterocycloalkyl, aryl and heteroaryl are optionally substituted with one or more halogen, CN, alkyl, alkoxy, haloalkyl, hydroxyalkyl, hydroxy, or oxo;
or R⁸ and R⁹ together with the nitrogen to which they are attached to form a heterocycloalkyl or heteroaryl, wherein heterocycloalkyl and heteroaryl are optionally substituted with one or more halogen, CN, alkyl, alkoxy, haloalkyl, hydroxyalkyl, hydroxy, or oxo;
with the proviso that R⁸ and R⁹ are not both hydrogen;
to a compound of formula (VI) or pharmaceutically acceptable salts thereof

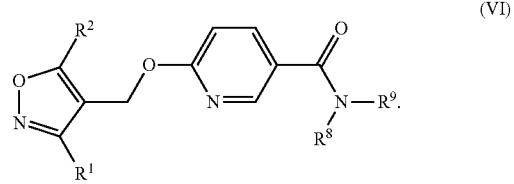

* * * * *